(12) United States Patent
Muzykantov et al.

(10) Patent No.: US 11,123,441 B2
(45) Date of Patent: Sep. 21, 2021

(54) METHODS AND COMPOSITIONS FOR DRUG DELIVERY

(71) Applicants: The Trustees of the University of Pennsylvania, Philadelphia, PA (US); The Regents of the University of California, Oakland, CA (US)

(72) Inventors: Vladimir Muzykantov, Bryn Athyn, PA (US); Jacob Brenner, Princeton Junction, NY (US); Jacob Myerson, Clayton, MO (US); Daniel Pan, Philadelphia, PA (US); Samir Suresh Mitragotri, Lexington, MA (US)

(73) Assignees: The Trustees of the University of Pennsylvania, Philadelphia, PA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/722,583

(22) Filed: Oct. 2, 2017

(65) Prior Publication Data
US 2018/0243440 A1    Aug. 30, 2018

Related U.S. Application Data

(60) Provisional application No. 62/403,764, filed on Oct. 4, 2016.

(51) Int. Cl.
*A61K 9/00*    (2006.01)
*A61K 47/69*    (2017.01)
(Continued)

(52) U.S. Cl.
CPC ........ *A61K 47/6901* (2017.08); *A61K 31/137* (2013.01); *A61K 31/573* (2013.01);
(Continued)

(58) Field of Classification Search
CPC .................................................. A61K 47/6901
See application file for complete search history.

(56) References Cited

U.S. PATENT DOCUMENTS 4,652,449 A    3/1987  Ropars et al.
8,329,161 B2   12/2012 Huang
(Continued)

FOREIGN PATENT DOCUMENTS

WO    WO-2015179602 A1    11/2015

OTHER PUBLICATIONS

Li, Lysoyme-Dextran-Core-Shell Nanogels Prepared ia a Green Process, Langmuir, 2008, 24, 3486-3492.*
(Continued)

*Primary Examiner* — Paul W Dickinson
(74) *Attorney, Agent, or Firm* — Howson & Howson LLP

(57) ABSTRACT

Compositions comprising a red blood cell (RBC) having non-toxically coupled thereto a nanoparticle having a low shear modulus or low Young's modulus of less than 10 MPa and containing a drug are provided. In one embodiment, the nanoparticles are optionally coated with protein. In another embodiment, the nanoparticle has no cell-specific targeting moiety or tissue-specific targeting moiety or organ-specific targeting moiety associated therewith. Methods of delivering selected drugs to target organs use these compositions both in vivo and ex vivo treatment of disease and for imaging.

19 Claims, 22 Drawing Sheets

(51) Int. Cl.
| | |
|---|---|
| A61K 47/61 | (2017.01) |
| A61K 47/64 | (2017.01) |
| A61K 38/18 | (2006.01) |
| A61K 51/12 | (2006.01) |
| A61K 49/00 | (2006.01) |
| A61K 31/137 | (2006.01) |
| A61K 31/573 | (2006.01) |
| A61K 47/68 | (2017.01) |

(52) U.S. Cl.
CPC .............. *A61K 38/18* (2013.01); *A61K 47/61* (2017.08); *A61K 47/64* (2017.08); *A61K 47/643* (2017.08); *A61K 47/6843* (2017.08); *A61K 47/6849* (2017.08); *A61K 47/6903* (2017.08); *A61K 47/6911* (2017.08); *A61K 47/6913* (2017.08); *A61K 47/6935* (2017.08); *A61K 49/0073* (2013.01); *A61K 49/0097* (2013.01); *A61K 51/1203* (2013.01); *A61K 51/1213* (2013.01); *A61K 51/1244* (2013.01)

(56) References Cited

U.S. PATENT DOCUMENTS

| | | | |
|---|---|---|---|
| 8,333,973 | B2 | 12/2012 | Muzykantov et al. |
| 8,734,787 | B2 | 5/2014 | Magnani et al. |
| 9,421,194 | B2 | 8/2016 | Prud'homme et al. |
| 2009/0274630 | A1 | 11/2009 | Huang |
| 2010/0061937 | A1 | 3/2010 | Magnani et al. |
| 2010/0285015 | A1 | 11/2010 | Muzykantov et al. |
| 2011/0008304 | A1 | 1/2011 | Troyer et al. |
| 2011/0250134 | A1 | 10/2011 | Cabrales et al. |
| 2011/0262466 | A1 | 10/2011 | Muzykantov et al. |
| 2011/0268803 | A1 | 11/2011 | Prud'homme et al. |
| 2012/0141540 | A1 | 6/2012 | Magnani et al. |

OTHER PUBLICATIONS

Ferrer, ICAM-1 Targeted Nanogels Loaded with Dexamethasone Alleviate Pulmonary Inflammation, PLOS One, 2014, 9(7), 1-7.*
Brenner, J. S., et al. Endothelial nanomedicine for the treatment of pulmonary disease. Expert Opin Drug Deliv. Feb. 2015;12(2):239-61. Epub Nov. 14, 2014.
Brochu H, Vermette P. Young's Moduli of Surface-Bound Liposomes by Atomic Force Microscopy Force Measurements. Langmuir. Mar. 4, 2008;24(5):2009-14. Epub Jan. 17, 2008.
Dunér G, et al. Quartz Crystal Microbalance with Dissipation (QCM-D) studies of the viscoelastic response from a continuously growing grafted polyelectrolyte layer. J Colloid Interface Sci. Oct. 15, 2013;408:229-34. Epub Jul. 19, 2013.
Kuebler, W. M. & Goetz, A. E. The marginated pool. Eur Surg Res. Jan.-Apr. 2002;34(1-2):92-100.
Oral I, et al. Measuring the Young's modulus of polystyrene-based composites by tensile test and pulse-echo method. Polymer Bull. Dec 2011;67(9):1893-1906.
Ahmed, EM, Mar. 2015, "Hydrogel: Preparation, Characterization, and Applications: A Review", J. Adv. Res., 6(2):105-121 (online publ. Jul. 2013).
Anselmo, A. C. & Mitragotri, S. Cell-mediated delivery of nanoparticles: taking advantage of circulatory cells to target nanoparticles. J. Control. Release 190, 531-541 (Sep. 2014).
Anselmo, A. C. et al., Delivering nanoparticles to lungs while avoiding liver and spleen through adsorption on red blood cells, ACS Nano, Nov. 2013, 7(12): 11129-11137.
Armstead, W. M. et al. RBC-coupled tPA Prevents Whereas tPA Aggravates JNK MAPK-Mediated Impairment of ATP- and Ca-Sensitive K Channel-Mediated Cerebrovasodilation After Cerebral Photothrombosis., Transl. Stroke Res. 3, 114-121 (Mar. 2012).
Berkhemer, OA et al, "A Randomized Trial of Intraarterial Treatment for Acute Ischemic Stroke", N Engl J Med. Jan. 1, 2015;372(1):11-20.
Brenner, J. S. et al. Mechanisms that determine nanocarrier targeting to healthy versus inflamed lung regions. Nanomedicine (May 2017). doi:10.1016/j.nano.2016.12.019.
Chu, D. et al. Nanoparticle Targeting of Neutrophils for Improved Cancer Immunotherapy. Adv. Healthc. Mater. 5(9): 1088-1093 (May 2016).
Dimitrakopoulos et al, Squeezing Motion of Capsules and Erythrocytes in Microfluidic Channels and Vascular Capillaries, Grant Abstract on www.grantome.com/grant/NSF/CBET-1335766 (2013).
Eckmann DM, et al., Nanogel Carrier Design for Targeted Drug Delivery. J Mater Chem B Mater Biol Med (Dec. 2014);2(46):8085-8097.
Ferrer, M. C. C. et al., Icam-1 targeted nanogels loaded with dexamethasone alleviate pulmonary inflammation, PLoS One, Jul. 2014, 9(7): e102329.
Gustafson, H. H., et al. Nanoparticle Uptake: The Phagocyte Problem. Nano Today 10, 487-510 (Aug. 2015).
Harisa, G. I. et al., Pravastatin chitosan nanogels-loaded erythrocytes as a new delivery strategy for targeting liver cancer, Saudi Pharmaceutical Journal, Jan. 2016, 24(1):74-81 (online pub Mar. 2015).
Hood, E. D. et al. Antioxidant protection by Pecam-targeted delivery of a novel NADPH-oxidase inhibitor to the endothelium in vitro and in vivo. J. Control. Release 163, 161-169 (Oct. 2012).
Hwang MR et al,. Gentamicin-Loaded Wound Dressing With Polyvinyl Alcohol/Dextran Hydrogel: Gel Characterization and in Vivo Healing Evaluation. AAPS PharmSciTech Sep. 2010; 11(3):1092-1103.
Liang X, et al. Mechanical properties and stability measurement of cholesterol-containing liposome on mica by atomic force microscopy. J Coll Interface Sci (Oct. 2004);278:53-62.
Luk, B. T. et al., Safe and Immunocompatible Nanocarriers Cloaked in RBC Membranes for Drug Delivery to Treat Solid Tumors, Theranostics, Apr. 2016, 6(7):1004-1011.
Pan, D. et al., The Effect of Polymeric Nanoparticles on Biocompatibility of Carrier Red Blood Cells, PLOS One, Mar. 2016, 11(3): e0152074.
Pan, D. et al., Red Blood Cell-Mediated Delivery of Lysozyme Dextran Nanogels to Pulmonary Vasculature, BMES 2016 Abstract P-Th-503, (Aug. 2016).
Scarcelli G, et al. Noncontact three-dimensional mapping of intracellular hydromechanical properties by Brillouin microscopy. Nature Methods (Dec. 2015); 12(12):1132-1134.
Schneberger, D., Aharonson-Raz, K. & Singh, B. Pulmonary intravascular macrophages and lung health: what are we missing? Am. J. Physiol. Lung Cell. Mol. Physiol. 302, L498-503 (Jan. 2012).
Tan, S. et al., Cell or Cell Membrane-Based Drug Delivery Systems, Theranostics, Apr. 2015, 5(8): 863-881.
Wiley, D. T., et al. Transcytosis and brain uptake of transferrin-containing nanoparticles by tuning avidity to transferrin receptor. Proc. Natl. Acad. Sci. U. S. A. 110, 8662-8667 (May 2013).

* cited by examiner

METHODS AND COMPOSITIONS FOR DRUG DELIVERY

CROSS-REFERENCE TO RELATED APPLICATIONS

This application claims the benefit of the priority of U.S. Provisional Patent Application No. 62/403,764, filed Oct. 4, 2016, which application is incorporated herein by reference.

STATEMENT REGARDING FEDERALLY SPONSORED RESEARCH OR DEVELOPMENT

This invention was made with government support under grant numbers HL121134 and HL125462 awarded by the National Institutes of Health. The government has certain rights in the invention.

BACKGROUND OF THE INVENTION

Most drugs fail in clinical trials because of dose-limiting off-target side effects. The field of "targeted drug delivery" aims to overcome that problem by putting drugs into carriers that deliver the drugs directly to the target organ. To achieve very high concentrations of the drug in the target organ, by far the most common effective method is to conjugate the carrier to a "targeting moiety" that binds to the target organ, such as antibodies which bind the target organ. There are multiple difficulties with using targeting moieties like antibodies, which must be tested in various animal species in clinical trials and then changed to include human epitopes and other humanized regions for further evaluation in humans. Additionally, antibodies can cause immunological reactions, especially when clustered in large numbers on a nano-scale drug carrier.

Drug delivery by nanocarriers (NCs) has been limited by difficulty delivering to most target organs, very high liver uptake, and the necessity of affinity moieties. For decades, the field of nanomedicine has held the promise of being able to deliver drugs directly to individual organs to avoid the off-target side effects which hinder most drugs. However, this basic idea, well-described by Paul Ehrlich more than a century ago, has run into numerous challenges. First, has been the challenge of high uptake of nanocarriers (NCs) in the liver and spleen, as part of the reticulo-endothelial system (RES)[28]. For most intravascularly injected NCs, the majority of the NC ends up in the liver, potentially causing a new side effect, hepatotoxicity. The second challenge is that nanomedicine is not able to achieve strong drug delivery to most organs, most notably the heart and brain, which account for a very large fraction of deaths. For example, highly optimized nanomedicine formulations whose target is the brain have total brain uptake values of at best 1% of the injected dose (% ID)[29]. Finally, for organ targeting, nanomedicine has had to rely on affinity moieties such as antibodies, have numerous translational challenges, such as inducing complement fixation when multiplexed on NCs and the common necessity of switching affinity moieties between each species tested because of low cross-species immunoreactivity. All of these problems have resulted in very few nanomedicine therapies directly targeting an organ, which was originally, and remains, the raison d'etre of nanomedicine.

Several diseases could benefit from targeted drug delivery, e.g., ischemic stroke immediately after embolectomy, to deliver drugs that limit ischemia reperfusion injury (IRI) and neuroprotectant drugs; myocardial infarction immediately after reperfusion to deliver IRI drugs; and acute lung diseases such as acute respiratory distress syndrome (ARDS). The need for targeted drug delivery in these diseases is well-illustrated by the case of ARDS. ARDS is an acute, diffuse, inflammatory lung injury with a variety of causes, most commonly pneumonia and sepsis. ARDS causes the lungs' air sacs, called alveoli, to fill up with proteinaceous liquid, preventing the lungs from oxygenating the blood. The impact of ARDS is enormous, with 190,000 US cases per year, and a mortality rate of 35%. Decades of research have yielded myriad drug targets, but after the failure of more than a dozen large clinical trials, there are still no FDA approved drugs that improve survival in ARDS. From a pharmacology perspective, there are three reasons why many rationally chosen drugs have failed in ARDS. Firstly, ARDS patients are too fragile to tolerate drug side effects. These patients have multi-organ dysfunction, and thus cannot tolerate even mild side effects. Secondly, the inhalational route of delivery, useful for so many pulmonary problems, has limited benefit in ARDS, as the flooded alveoli (those filled with liquid) are covered by a column of fluid, which means that topical delivery to the alveoli is not possible via the inhaled route. Finally, ARDS is a very heterogeneous disease, so targeting a single pathway is unlikely to be sufficient. Still other diseases requiring drug delivery to the brain, as well as other targeted cells, also require new modes of delivery.

Various leukocytes, platelets, and RBCs have been used to shuttle NCs to target organs[30,31]. However, most of these approaches have produced relatively modest uptake in the target organ and have led to significant side effects. Red blood cells (RBCs) are promising tools for vascular drug delivery due to their long circulation time, high degree of mechanical flexibility that allows passage through capillary blood vessels, and significant time spent in contact with the vessels. Previous studies have explored the use of RBCs for delivery of physisorbed rigid nanoparticles to the endothelium[1]. Nonetheless, contact of RBCs with non-biological objects such as nanoparticles can adversely alter RBC integrity and vascular behavior.

A continuing need in the art exists for new and effective tools and methods for drug delivery to tissues and organs, including the lung and brain.

SUMMARY OF THE INVENTION

The needs of the art are met in the methods and compositions disclosed herein. In one embodiment, these methods and compositions provide an advantage of delivering drugs via the intravascular route to the lungs, shuttling potentially multiple drugs to the inflamed alveoli. In other embodiment, similar vascular drug delivery methods and compositions are provided which permit intravascular drug delivery for other diseases. These compositions described herein provide a drug carrier that can massively increase drug concentration in an organ in a manner independent of antibodies.

In one aspect, a composition comprises a red blood cell (RBC) having biocompatibly coupled thereto a nanoparticle having a low shear modulus or low Young's modulus of less than 10 MPa and containing a drug. In another embodiment, the low shear modulus is less than 1 MPa. In one embodiment, the nanoparticle has a highly hydrophilic exterior. In another embodiment of this composition, the nanoparticle is coated with a biomolecule, e.g., a protein, that does not induce any severe or untolerable adverse reaction, e.g., immunological reaction, to the any component of the composition in a mammalian subject. In still another embodiment, of this aspect, the composition is useful as an intravenous or intraarterial drug delivery system that can shuttle one or multiple drugs specifically to targeted tissue or organs, thereby eliminating the off-target effects of the loaded drugs.

In another aspect, a composition for the treatment of ARDS comprises an isolated red blood cell (RBC) having non-toxically coupled thereto a nanoparticle having a shear modulus or a Young's modulus of less than 10 MPa, said nanoparticle containing a drug selected from one or more of albuterol, dexamethasone, palifermin, or other drugs previously shown to aid in the treatment of ARDS but that have significant off-target side effects. In one embodiment, the low shear modulus is less than 1 MPa.

In still another aspect, a method for delivering a drug to a mammalian subject comprises administering to a subject having a disease a composition comprising a red blood cell having non-toxically coupled thereto a nanoparticle having a low shear modulus or low Young's modulus of less than 10 MPa and containing a drug. In one embodiment, the low shear modulus is less than 1 MPa. The nanoparticles are transferred from the composition to the cells of the subject and release the drug in vivo where it accumulates in a targeted solid organ via a vascular feed.

In still another aspect a method of imaging a mammalian organ comprises injecting intravenously or intraarterially in vivo or ex vivo a composition comprising a red blood cell (RBC) having biocompatibly and/or non-toxically coupled thereto a nanoparticle having a low shear modulus or low Young's modulus of less than 10 MPa and containing an imaging agent. In one embodiment, the low shear modulus is less than 1 MPa. The nanoparticles are transferred from the RBC-flexible NP to the cells of the vascular bed of a subject, e.g., endothelial cells, WBCs and other cells, and release the imaging drug in a selected target organ or tissue.

In a further aspect, a method of making a nanoparticle comprises covalently bonding to a nanoparticle having a shear modulus or a Young's modulus of less than 10 MPa a protein that does not induce an immunological reaction to the nanoparticle in a mammalian subject. In one embodiment, the low shear modulus is less than 1 MPa. Additional steps wherein the nanoparticle is a hydrogel include loading said nanoparticle with a suitable drug by incubation at 37° C. in buffer; and non-toxically adsorbing the loaded nanoparticles onto isolated RBC prior to delivery in vivo or ex vivo. Because nanogels have "burst release" (release their drug contents immediately upon being placed in a solution that does not contain the drug), in one embodiment, the nanogels are adsorbed onto RBCs with the drug in the solution.

In another aspect, a method involves delivering a nanoparticle having dual affinity. As an example, the nanoparticle liposome has attached to it an anti-RBC antibody and an anti-target antibody. The anti-target antibody can be an antibody directed to an antigen expressed on the target cell. In one embodiment, the antigen on an endothelial cell is ICAM. The nanoparticle associated with both antibodies demonstrates the ability to bind both the RBC delivery agent and the ultimate target, e.g., the EC.

Still other aspects and advantages of these compositions and methods are described further in the following detailed description of the preferred embodiments thereof.

BRIEF DESCRIPTION OF THE DRAWINGS

As illustrated in FIG. 18A, a short biotin linker was used, and after injection in mice, only cargo protein partially detached from carrier RBC and was transferred to the pulmonary vasculature. In FIG. 18B, a long biotin linker was used, and both streptavidin and cargo protein were detached from carrier RBC and transferred to the pulmonary vasculature. Pulmonary vasculature indicated by rectangular bars labeled EC in inset cartoon. The difference in between the short spacer and the long spacer is a chain of —CH$_2$—. The short spacer arm is ~20 Angstrom and the long spacer is ~30 Angstrom. As there are two different points of biotinylation (i.e., connecting the NP to the SA and connecting the SA to the RBC) the longer spacer arms make a total of 60 Angstrom, while the shorter around 40 Angstrom. These longer spacer arms give more flexibility for interactions. Percentage of injected dose (% ID) is plotted in the bar graphs.

DETAILED DESCRIPTION

Figure 1:
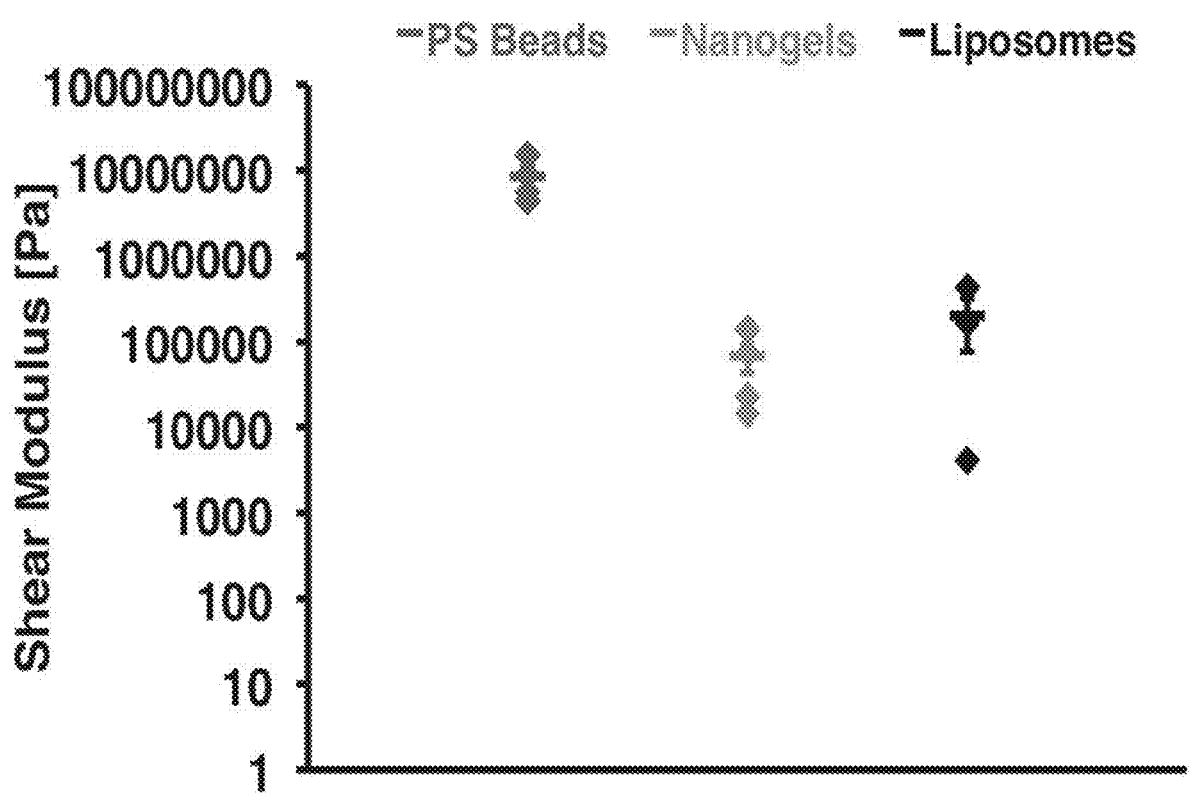
FIG. 1 is a graph showing that polystyrene (PS) beads are much harder than hydrogels (nanogels) or liposomes, as measured in shear modulus in Pascal units.

The compositions and methods described herein demonstrate the development and use of novel drug delivery compositions and methods involving biocompatibly coupling, e.g., adsorbing, a pharmaceutical agent onto a RBC, followed by intravascular injection of the RBC-adsorbed agents in order to cause accumulation of the agent in the organs downstream of the injection. The "pharmaceutical agents" can be nano-scale drug carriers (e.g., liposomes or nanogels), drugs (including antibodies, proteins, peptides, and small molecule drugs), gene therapy vectors (such as viruses, engineered bacteria, or synthetic vectors), diagnostic agents (e.g., to assess disease status using an imaging modality), any other agent which may be clinically useful to accumulate in a target organ.

The problems with red blood cell (RBC)-hitchhiking (RH) are overcome by resort to the compositions and methods described herein. NCs are first adsorbed onto RBCs and then when injected intravascularly, the NCs are transferred to the first downstream organ. With low-shear-modulus NCs such as liposomes and nanogels, RH achieves 14.4× more uptake in the lung compared to free NCs. RH delivers even more impressively to the brain, with a brain:liver ratio 133× higher than free NCs, outperforming leading affinity moieties by more than an order of magnitude. Showing broad applicability, the examples below demonstrate that RH works for most clinically relevant NCs and nanoscale viral vectors, and that it works in mice, pigs, and in ex vivo human lungs, without end organ toxicities. Thus, RH is a clinically translatable platform technology poised to augment drug delivery in acute lung disease, stroke, and several other diseases.

In one aspect, the inventors provide a composition in which the pharmaceutical agent is a nanoparticle having a low shear modulus or low Young's modulus and containing one or more drugs, the nanoparticle being biocompatibly coupled to a red blood cell (RBC). In one embodiment, the low shear modulus is less than 1 MPa. In another embodiment, the low shear modulus is less than 10 MPa. In one aspect described herein, and after years of research, the inventors describe flexible nanoparticles for use in the delivery of one or a multiple of drugs or reagents to a mammalian vascular bed, e.g., endothelial cells, WBC or other cells of a tissue or an organ for therapeutic, prophylactic and diagnostic purposes. In one embodiment, use of this composition employs vascular addressing, i.e., delivery of the RBC-NP coupled composition through a vascular bed, to ensure accumulation of the nanoparticle, and thus the drug, in the vascular endothelium, or in or on WBC or other cells, or elsewhere within the first end-organ after the point of injection, or the first end-organ itself.

By "nanoparticle" or "NP" (also referred to as "nanocarrier" or "NC") as used herein is meant a particle having diameter of between 1 to 1000 nm. In one embodiment the NP is globular. Inclusive in this definition are particles with a diameter of at least 1, at least 20, at least 40, at least 60, at least 80, at least 100, at least 120, at least 140, at least 160, at least 180, at least 200, 220, at least 240, at least 260, at least 280, at least 300 nm in diameter. In other embodiments, also included are particles having diameters of at least 320, at least 340, at least 360, at least 380, at least 400, at least 420, at least 440, at least 460, at least 480, at least 500, 520, at least 540, at least 560, at least 580, at least 600, 620, at least 640, at least 660, at least 680, at least 700 nm. In yet other embodiments, also included are particles having diameters of at least 720, at least 740, at least 760, at least 780, at least 800, at least 820, at least 840, at least 860, at least 880, at least 900, 920, at least 940, at least 960, at least 980, up to at least 1000 nm. All numbers and fractions between any two of these numbers are also included.

By "flexible" or "soft" nanoparticles or "nanoparticles having a low shear modulus" as used herein is meant nanoparticles having an NP diameter as specified above and having a low shear modulus/low Young's modulus, which based on QCM (quart crystal microbalance). In one embodiment, the flexible nanoparticle is defined as less than 10 megaPascal (MPa) and containing one or more selected drugs. In another embodiment, the flexible nanoparticle is defined as less than 1 megaPascal (MPa) and containing one or more selected drugs. In still other embodiments, the flexible nanoparticle is defined as less than 2, 3, 4, 5, 6, 7, 8, 9 or 10 MPa and containing one or more selected drugs. In one embodiment, a soft NP is a hydrogel NP (also referred to as a nanogel or NG). In another embodiment, a soft NP is a liposome. As discussed herein, the inventors have determined experimentally that soft NPs are less toxic to RBCs than hard NPs. Also as determined experimentally by the inventors, soft nanoparticles (NPs) accumulate in the first end-organ much more efficiently than hard NPs. In one embodiment, lysozyme-dextran nanogels (lysozyme-dextran nanogels) as flexible or soft nanoparticles provide a unique combination of superior compatibility with RBCs and strong delivery to pulmonary vasculature.

In contrast, rigid NPs, such as bulk polystyrene, are reported to have a Young's modulus of ~3 GPa. See, e.g., Oral I, Guzel H, Ahmetli G. Measuring the Young's modulus of polystyrene-based composites by tensile test and pulse-echo method. Polymer Bulletin 2011; 67(9):1893-1906. Other suitable pharmaceutical agents, in place of a nanoparticle can be a multimolecular protein conjugate.

Thus, in one embodiment, the NP used in the compositions is a nanogel. By "hydrogel nanoparticle" or "nanogel" as used herein is mean a polymeric material having a hydrophilic structure which renders it capable of holding amounts of selected drug compounds in their three dimensional networks, the resulting particle having nanoparticle dimensions. Macroscopic dextran hydrogels have shown Young's moduli of ~10-50 kPa in the literature. See, e.g., Hwang M R, Kim J O, Lee J H, Kim Y I, Kim J H, Chang S W, Jin S G, Kim J A, Lyoo W S, Han S S, Ku S K, Yong C S, Choi H G. Gentamicin-Loaded Wound Dressing With Polyvinyl Alcohol/Dextran Hydrogel: Gel Characterization and In vivo Healing Evaluation. AAPS PharmSciTech 2010; 11(3):1092-1103. In one specific embodiment, a soft NG is a lysozyme-dextran nanogel (also referred to as LDNG). In one embodiment the LDNG is a synthetic contruct of lysozyme and dextran. In other embodiments, a nanogel is made of chitosan or chitin, pullulan, hyaluronic acid, PEG, pluronics (e.g. F127), poly(acrylic acid) or poly(acrylate), poly(oligo(ethylene glycol)methyl ether methacrylate), poly (ethylene oxide), polyethylenimine, poly(caprolactone), and poly(N-isopropylacrylamide), among other options encompassing a wide range of hydrophilic polymers capable of chemical modifications enabling incorporation in a nanoparticle. See, e.g., Eckmann D M, Composto R J, Tsourkas A, Muzykantov V R. Nanogel Carrier Design for Targeted Drug Delivery. J Mater Chem B Mater Biol Med 2015; 2(46): 8085-8097; and Ahmed E M, March 2015, "Hydrogel: Preparation, Characterization, and Applications: A Review", J. Adv. Res., 6(2):105-121, among other publications in the art. In certain embodiments described herein nanogel particles containing a drug and associated with an RBC behave best in this form of drug delivery. Compared to rigid or hard polystyrene beads, nanogels (e.g., lysozyme-dextran nanogels) also show improved RBC physisorption efficiency, decreased hemolysis, decreased RBC aggregation, and improved delivery to the lungs.

In still other embodiments the nanogel or NP has a carbohydrate surface which aids with RBC and endothelial glycocalyx interaction. In another embodiment, the protein coating, e.g., IgG or albumin, prevents RBC toxicity and aids RBC adsorption. In yet another embodiment, the protein-coated nanogels are cross-linked or lyophilized. In still another embodiment, the nanogel or flexible NP has a capacity sufficient for large drugs or imaging agents.

In another aspect, the NP employed herein is a liposome. By "liposomes" as used herein is meant a material a microscopic spherical particle formed by a lipid bilayer enclosing an aqueous compartment. Certain liposomes have by AFM, exhibited a Young's modulus of ~40 kPa in a modified Hertzian model. See, e.g., Brochu H, Vermette P. Young's Moduli of Surface-Bound Liposomes by Atomic Force Microscopy Force Measurements. Langmuir 2008; 24(5): 2009-2014. In another embodiment a liposome is defined by a Young's modulus of ~1-10 MPa in the standard Hertzian model. See, e.g., Liang X, Mao G, Ng S. Mechanical properties and stability measurement of cholesterol-containing liposome on mica by atomic force microscopy. J Coll Interface Sci 2004; 278:53-62.

In another embodiment, the nanoparticle for use in the compositions described herein does not induce an intolerable adverse reaction in a mammalian subject to any component of the composition. In another embodiment, the nanoparticle is coated with a biomolecule that also does not induce an intolerable adverse reaction, such as an immunological reaction to the nanoparticle composition in a mammalian subject. Among suitable biomolecules are proteins that are substantially immunologically inert to mammalian subjects, particularly humans, are human albumin, bovine serum albumin, and immunoglobulin G. Other proteins that do not provoke immunological reactions in the recipient subject, may also be employed to coat the selected flexible NPs, e.g., nanogels or liposomes.

In yet another embodiment, a suitable nanoparticle for use in the compositions described herein has no cell-specific targeting moiety or tissue-specific targeting moiety or organ-specific targeting moiety associated therewith. As an example, the composition comprising the RBC and NP is not associated with any targeting moiety such as an antibody to a tissue cell surface protein.

Figure 16:
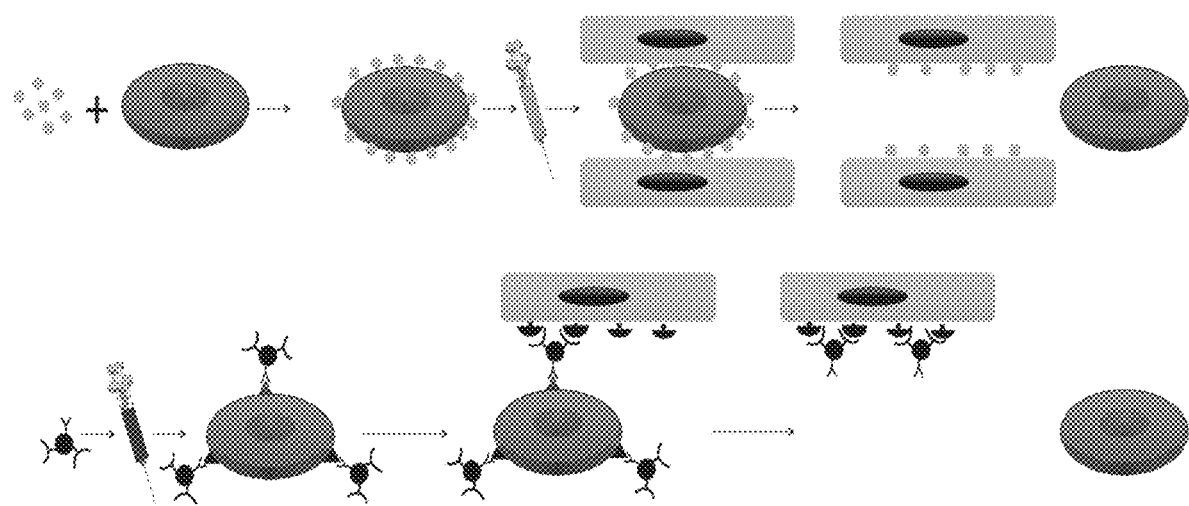
FIG. 16 is a cartoon showing two main modes for RH application, namely physical absorbtion of NCs on carrier RBC (top panel) and dual targeting of the nanoparticles to the target endothelial cell (EC) or other cell (bottom panel). The top panels shows nanoparticle (small dots) which are bound onto the isolated RBC and injected as the RBC/NP complex into the subject, where the RBC carrying NP becomes squeezed between vascular (e.g., endothelial) cells in the microcirculation area downstream the injection site, and the nanoparticles then are transferred to these vascular cells (e.g., endothelial cells) in the target organ. In contrast, the lower panel shows nanoparticles coated with antibody (Y shape) to RBC and with antibody to an EC target antigen, such as ICAM (curve shape on a stem). Such dual-targeted NP can be injected intravascularly without the need for loading to isolated RBC. The NP will bind rapidly to circulating RBC due to the presence of anti-RBC antibody on the NP. When RBC carrying such dual-targeted NP comes into the contact with counterpart vascular cells in the target organ (predominantly ECs), the anti-ICAM antibody links the nanoparticle to the EC, and the nanoparticle is transferred to the target.
Figure 17:
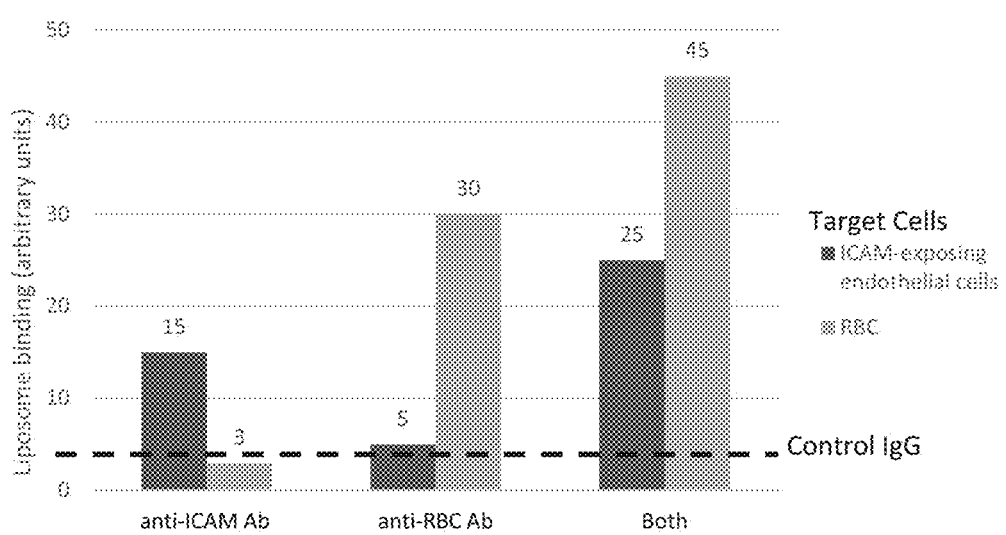
FIG. 17 is a bar graph showing the results of a study in which (1) liposomes have been coated by antibody to RBC (middle pair) or (2) liposomes have been coated by antibody to endothelial antigen ICAM (left pair), or (3) liposomes have been coated by antibody to both RBC and ICAM (right pair) or (4) control IgG (dashed line). The binding of liposomes (measured by arbitrary liposome binding units) was tested to ICAM-exposing endothelial cells (dark bars) or RBC (light gray bars). This result illustrates that liposomes coated with affinity ligands—either single, anti-RBC or anti-EC, or dual, do bind respectively to either single target cell (RBC or EC, correspondingly), or to both cells.

In another embodiment, the composition containing the RBC and coupled NP optionally has associated targeting moieties directing the composition to the target organ or tissue, such as antibodies that bind to the organ's endothelium (e.g., antibodies targeting endothelial proteins including PECAM, ICAM, VCAM, transferrin receptor, and many more) or antibodies that bind to other targeted cells. See, e.g., FIG. 16.

Figure 18A:
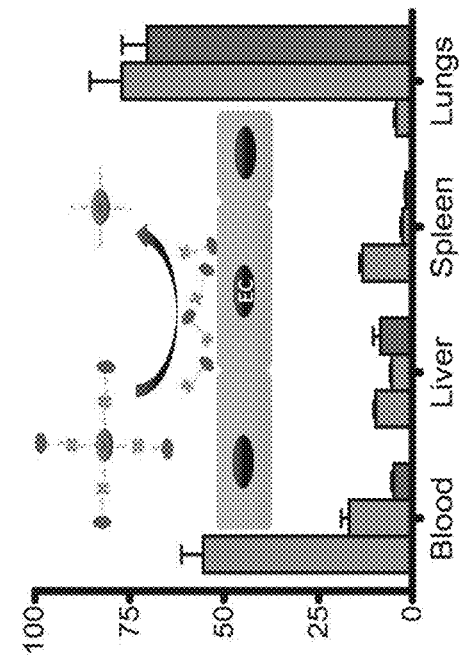
FIGS. 18A and 18B are two graphs showing that vascular transfer from RBC to vascular cells, first of all, endothelial cells (EC) or other recipient cells can be precisely modulated by the mode of coupling to carrier RBC, in particular the length of spacers in the molecular bridge between cargoes and RBC. In this experiment, RBC radiolabeled by $^{51}$Cr (leftmost bar in each tissue set in graph; and elliptical with dark nucleus in inset cartoon, b-RBC) were conjugated via biotin (b) linker with streptavidin (SA, middle bars in each set in graph; indicated by X shape in inset cartoon) labeled with a different isotope that was further conjugated via a biotin linker to a cargo protein (IgG) labeled by another isotope (rightmost bar in each tissue set in graphs; dark ovals in inset cartoon).
Figure 18B:
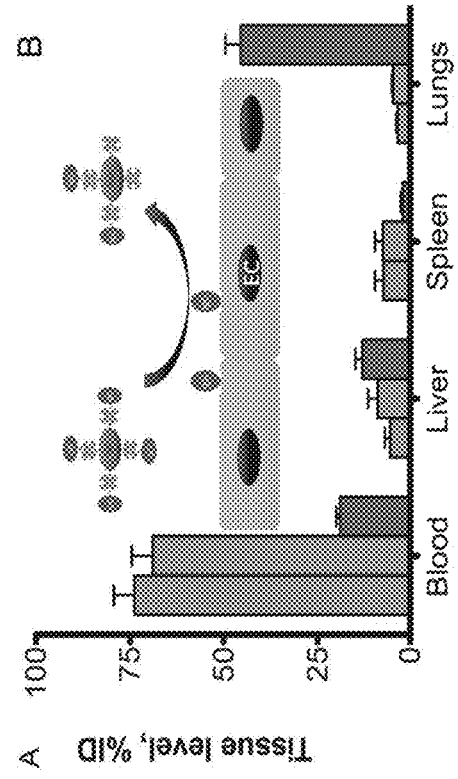

In another embodiment, the NPs with their drug cargoes are chemically conjugated to the surface of RBC using molecular cross-linkers, spacers, and bridges. By cross-linkers, spacer and bridges are meant any moiety used to attach or associate the NP to the RBC. Thus in one embodiment, the cross-linker is a covalent bond. In another embodiment, the linker is a non-covalent bond. In still other embodiments, the linker can be a larger compound or two or more compounds that associate covalently or non-covalently. In still other embodiment, the linker can be a combination of the linkers, e.g., chemical compounds, nucleotides, amino acids, proteins, etc. In one embodiment, the cross-linker is biotin-streptavidin. In this embodiment, interconnecting molecule(s) such as streptavidin can be coupled to RBC either directly via chemical modification, or via biotin derivatives conjugated to the functional groups on RBC, inserted into RBC phospholipids or coupled to other appropriate RBC components such as sugars, with or without additional spacers between the active group anchoring biotin derivative to RBC. In turn, cargo molecules are coupled to streptavidin either via chemical conjugation or via using biotin derivatives as described above. In one embodiment a spacer is positioned between biotin and a reactive group, such as succinimide ester group. In certain embodiments, a spacer version is a polyethylene glycol (PEG) chain with MW from ~100 daltons (D) to up to 10,000 D. In another embodiment, the spacer is an aliphatic chain —$CH_2$—$CH_2$—$CH_2$— with size varying from 1 angstroms (A) up to 5, 10, 15, 20, 25 or 30 Angstroms. In FIGS. 18A and 18B, the difference between the short spacer and the long spacer is a chain of —$CH_2$—. The short spacer arm is ~20 Angstrom and the long spacer is ~30 Angstrom. As there are two different points of biotinylation in the constructs of the figures, the longer spacers make a total of 60 Angstrom, while the shorter around 40 Angstrom. Longer spacer arms give more flexibility for interactions. In another embodiment the linker is composed of at least one to about 25 atoms. In still another embodiment, the cross-linker is formed of a sequence of at least 2 to 60 nucleic acids. In yet another embodiment, the cross-linker refers to at least one to at least 2, up to about 30 amino acids or 1 or more proteins within that size.

The selected NPs for use in this invention are pre-loaded before coupling to the RBC with one or more selected drugs. In one embodiment, the NP loading is high capacity, e.g., the mass of the drug is >5% the mass of the NP. In one embodiment the selected NP contains a single drug component. In another embodiment, the selected NP is loaded with multiple drug components. By "drug" as used herein is meant any therapeutic, prophylactic or diagnostic compound or reagent that is contained within the flexible nanoparticles described herein. In one embodiment, the drug is a water-miscible compound. In another embodiment an anti-rejection drug. Anti-rejection drugs include agents such as alemtuzumab, tacrolimus, and other drugs currently delivered systemically post-transplant to prevent rejection. In another embodiment, the drug is an anti-inflammatory agent. Anti-inflammatory agents include corticosteroids, methotrexate, mycophenolate mofetil, azathioprine and other agents intended to limit inflammation. In another embodiment, the drug is a pro-angiogenic factor, such as VEGF-receptor agonists and other known such factors. In another embodiment, the drug is an anti-edema agent, e.g., albuterol. In still another embodiment the drug is a compound that prevent ischemia-reperfusion injury, such as N-acetylcysteine, allopurinol, L-arginine, among known agents.

In a specific example, where the composition is designed for the improvement of ARDS, in one embodiment, multiple drugs are employed in the NPs. These drugs include combinations that act on multiple cell types, such as albuterol (acting on epithelial ENac to pump out alveolar fluid), dexamethasone (enhances endothelial barrier function and decreases neutrophil activity), and palifermin (enhances repair and regeneration of alveoli). Other drug combinations with possible applications in other diseases include but are not limited to: Imatinib Mesylate (trade name Gleevec, a tyrosine kinase inhibitor approved for treatment of a variety of cancers), EUK-134 (a superoxide dismutase and catalase mimetic capable of mediating oxidative stress injury), MJ33 (an NADPH oxidase inhibitor used for antioxidant protection). Still other drug(s) or combinations for loading in the NPs of these compositions may be selected from among libraries of drugs for a variety of diseases.

In still another embodiment, the drug is an imaging agent. Among suitable imaging agents are molecules containing radionuclides that are amenable to SPECT or PET imaging (e.g., Indium-111 for SPECT imaging); molecules containing moieties that provide contrast for CT imaging (e.g., gold nanoparticles or iodinated contrast agents); molecules containing moieties that provide contrast for MRI imaging (e.g., gadolinium);

nano- or micro-scale complexes that provide contrast for ultrasound imaging (e.g., microbubbles filled with gas).

In another aspect, a suitable nanoparticle for use in the methods herein is miscible with endothelial glycocalyx (e.g., carbohydrates on nanogel interdigitate with endothelial cells).

In another aspect, a suitable nanoparticle for use in the methods herein is characterized by release kinetics permitting greater than 50% of the drug load to be released within about 1 hour after administration in vivo. The drug release occurs via burst-release or activated release. Such release kinetics may be readily measured by incubating the NP in buffer (containing, for example, serum) at multiple temperatures (notably including 37° C.) and measuring the release of drug over time by separating the NP from the buffer (e.g., via centrifugation or chromatography), with the drug concentration being measured by tools such as HPLC (high performance liquid chromatography), LC-MS (liquid chromatography couple to mass spectrometry), etc. An example of this for a nanoparticle mentioned here, liposomes is Pippa, N et al, "Temperature-dependent drug release from DPPC:C12H25-PNIPAM-COOH liposomes: control of the drug loading/release by modulation of the nanocarriers' components.", Int J Pharm. 2015 May 15; 485(1-2):374-82.

In the compositions described herein, the nanoparticles are biocompatibly or non-toxically coupled with the RBC. In one embodiment of such biocompatible and/or non-toxic coupling, the NPs are physisorbed onto the RBCs. In this embodiment, there are no covalent bonds between the NP and RBC. Physisorption can either be mediated by several methods. In one method, the NP can adsorb onto the RBC in a manner that is "independent of an affinity moiety," which practically means that the NP sticks to the RBC because of "non-specific" (or unknown) surface properties of the NP. See FIG. 16, top panel. In the second embodiment of physisorption, the the NP can be coated with an "affinity moiety" such as an antibody or peptide that has a high affinity (typically in the 1-100 nM range) for an epitope on the RBC surface. See, FIG. 16 bottom panel. In one embodiment, nanoparticles coated with protein, whether soft (e.g., LDNGs) or hard (e.g., PS) that are coated with protein physisorb very well onto RBCs. In one example, when mixed with RBCs, protein-coated LDNGs will physisorb at 80% efficiency onto RBCs. By contrast, uncoated polystyrene nanoparticles of the same size only adsorb at 5-10% efficiency onto RBCs. In another embodiment, the NPs are chemisorbed to the RBC, in which covalent bonds are formed via a chemical reaction. This in one embodiment of the composition, the NP and RBC are coupled via covalent bonds. In still another embodiment the biocompatible coupling is affinity coupling. The toxicity of coupling NPs to RBCs can be measured via a large variety of tests, including hemolysis, agglutination, and susceptibility to osmotic or mechanical stress, as demonstrated in papers such as PLoS One. 2016 Mar. 22; 11(3):e0152074.

The biocompatible and/or non-toxic coupling or adsorption of the NP to the RBC in these compositions allows ready transfer of the NP from the RBC to the end target, e.g., vascular endothelium, WBC, or other cells of the end organ.

Without wishing to be bound by theory, the method operates in this manner: an RBC to which a NP is adsorbed or coupled transfers the NP to the surface of a vascular vessel, e.g., a capillary, due to mechanisms such as physical squeezing of the RBC through the capillary. In one embodiment, because RBC-NP coupled compositions are bigger than the pulmonary capillaries, the RBCs squeeze through the capillaries with their surface sliding along the surface. This causes the physisorbed NPs to be pressed against the vascular cells, resulting in internalization of the NPs into the endothelial cells and/or other intra-luminal cells, such as marginated neutrophils, WBC or other cells. This is one of multiple mechanisms responsible for the transfer of NPs to the downstream target organ. In one embodiment, the NP is a nanogel carrying one or more selected drugs for delivery to the the vessel.

In a method using dual-targeted NPs, i.e., in which the NP is associated with an antibody to RBC and an antibody to an antigen on the ultimate target cell, the delivery of the drug in the NP is aided by covalent binding of the NP to the RBC and then further targeting by the covalent binding of the antibody to the target antigen to the resulting target. The NP is thereafter taken by the target cell and the RBC released. See FIG. 16 lower panel.

These compositions comprising RBC coupled non-toxically to a drug-loaded flexible NP can be readily prepared by selecting a nanoparticle having a shear modulus or a Young's modulus of less than 10 MPa. In one embodiment, the low shear modulus is less than 1 MPa. The selected NP can be optionally coated with with a protein that does not induce an immunological reaction to the nanoparticle in a mammalian subject. By "mammalian subject" is meant primarily a human, but also domestic animals, e.g., dogs, cats; and livestock, such as cattle, pigs, etc.; common laboratory mammals, such as primates, rabbits, and rodents; and pest or wild animals, such as deer, rodents, rabbits, squirrels, etc. The selected coated or non-coated NP is then loaded with a suitable drug or multiple drugs generally by incubation at about 37° C. in a buffer. Desirable buffers are those that are RBC-compatible, such as phosphate buffered saline or the like. Other methods for drug loading in drug carriers physisorbed on RBCs include osmotic loading of a variety of small molecule drugs in protein, nanogel, or nanoparticle carriers either before or after physisorption of nanogels on RBCs, allowing burst release of loaded drugs in targeted vascular beds. Drug loading and release from nanogels on RBCs may be modified by using crosslinkers incorporated in the nanogel to prolong or enhance encapsulation of loaded drugs and performing the crosslinking after drug loading. Crosslinkers can include responsive moieties (e.g. enzyme-cleavable crosslinkers that allow stimulated drug release in response to protease activity). In another embodiment, the drug is kept in the solution or in the wash buffer during all drug loading steps (except the last resuspension).

Following drug loading, the NP is non-toxically adsorbed onto isolated RBC prior to delivery in vivo. In one embodiment, RBCs are isolated from a mammalian subject and subjected to adsorption with the NPs before or after leukoreduction. In another embodiment, no leukoreduction is performed. In one embodiment, the source of the RBC is a typed and crossmatched unit of peripheral RBCs. In another embodiment, the source of the RBC is a universal donor (O-neg).

Similarly the methods may employ other adjunctive steps or devices to prepare the compositions described herein including microfluidic devices to put RBCs and NGs into small volume to increase adsorption efficiency or storage of NGs in bags that are PRBC compatible, or use of bags that don't adsorb NPs, use of wide bore infusion tubing or tubing that doesn't adsorb nanoparticles, short-tubing to avoid adsorption to tubes or use of transfer pipettes (large bore) during wash steps.

In one embodiment, wherein the nanoparticle is a hydrogel, the preparative method can involve retaining adsorbed RBC-hydrogel nanoparticle in a solution containing a high concentration of the drug and centrifuging the adsorbed RBC and resuspending same in a solution with a low concentration of said drug within 60 minutes before in vivo delivery. In another method the adsorbing step can occur by adding loaded nanoparticles to a unit of red blood cells without excipients. In still another preparative method step, the adsorbing can involve extracting blood from a mammalian subject; agitating a mixture said loaded nanoparticles ex vivo within 60 minutes before in vivo delivery. In still a further modification of the preparative method, the loaded nanoparticles are present in a syringe and adsorbing occurs when a mammalian subject's blood is withdrawn into the syringe. In another embodiment, if a small volume of RBCs is used, the container may be pre-coated with RBCs before adsorption with NPs.

In another aspect, these compositions comprising an RBC coupled to a drug-loaded, flexible NP are useful in therapeutic treatment of disease, diagnosis of disease or prophylactic treatments to prevent disease, depending upon the identities of the drugs with with the NPs are loaded.

By "disease" as used herein is meant, without any limitation, any disease in which small arterioles, capillaries, or venules and/or the endothelial barrier plays an important role. Without limitation, such diseases and disorders include those involving the lung, including ARDS, IPF (idiopathic pulmonary fibrosis), pulmonary arterial hypertension, post-pulmonary embolism to prevent reactive vasoconstriction, pulmonary capilliaritis syndromes, such as the vasculitidies of granulomatosis and polyangitis (GPA) and Goodpasture's syndrome, among others. Still other diseases suitable for such treatment include those involving the heart, such as heart attack, ischemia-reperfusion injury, stroke or other diseases involving the heart; diabetic retinopathy or macular degeneration and other disorders involving the eye; hyperthyroidism or hypothyroidism and other diseases involving the thyroid; autoimmune hepatitis, alcoholic hepatitis, NAFLD/NASH and other diseases involving the liver; pancreatitis or other diseases of the pancreas; immunological disorders or other diseases of the spleen; inflammatory bowel disease and other diseases of the intestines; benign prostatic hypertrophy (BPH), prostate cancer, and other disease of the prostate; disorders of the brain and cancers of any organ or tissue. Still other diseases or conditions suitable for treatment, prophylaxis or diagnosis with compositions described herein include ischemic stroke, prevention of ischemia reperfusion injury (IRI), prevention of post-myocardial infarction, also for prevention of IRI, prevention or treatment of PAD (peripheral artery disease, especially the legs), prevention or treatment of cancer, especially head/neck cancer after subarachnoid hemorrhage, and encephalitis and meningitis. In still another embodiment, the disease or disorder may be a need for a transplanted organ, and the transplanted organ itself may be treated ex vivo with compositions described herein, e.g., to prevent IRI. This includes all solid organ transplants.

As one specific embodiment, a composition for the treatment of ARDS comprises an isolated red blood cell (RBC) having biocompatibly and/or non-toxically coupled thereto a nanoparticle having a shear modulus or a Young's modulus of less than 1 MPa or less than 10 MPa, said hydrogel containing a drug selected from one or more of albuterol, dexamethasone and palifermin. In one embodiment, the nanoparticle is a lysozyme-dextran hydrogel. In another embodiment, the nanogel is coated with albumin or IgG. Still other compositions directed toward treatment, prophylaxis or diagnosis of other diseases can be readily designed using the teachings contained herein.

Thus, in yet another aspect, a method for delivering a drug to a mammalian subject comprises administering to a subject having a disease a composition comprising a red blood cell having non-toxically coupled thereto a nanoparticle having a low shear modulus or low Young's modulus of less than 1 MPa or less than 10 MPa and containing a drug, wherein said nanoparticles are transferred from the composition to the cells of the subject and release the drug in vivo. In one embodiment, the drug is released from the nanoparticles within 60 minutes of administration in vivo. In another embodiment, the composition contains a single drug or multiple drugs. In another embodiment, multiple drugs are administered simultaneously in the same or multiple RBC-coupled NP compositions.

Administration of the RBC-adsorbed NP compositions described herein can be intravenously for delivery of the drug to the lungs. For example, where the disease is ARDS, pneumonia, interstitial lung disease, idiopathic pulmonary fibrosis, post-pulmonary embolism; pulmonary capilliaritis syndrome, or emphysema, the compositions may be administered i.v. In one embodiment, this method employs the injecting iv the compositions described herein carrying one or more of albuterol, dexamethasone, and palifermin for the treatment of ARDS.

For administration to any other organ, where the disease involves any other selected mammalian organ, the composition is administered in vivo intra-arterially immediately upstream of an organ for delivery of effective doses of the drug.

Additionally, for treatment of disease involving a selected mammalian organ designated for transplantation (other than the lung), the composition is administered ex vivo via feeding arterial opening into the organ prior to reperfusion and transplantation. In any intra-arterial administration, the composition can be administered via an intra-arterial catheter. Such organs include, without limitation, the heart, brain, eyes, thyroid, kidney, liver, pancreas, spleen, intestines, or prostate.

Certain adjunctive steps for administering the compositions described herein include rotating or agitating or diffusing the RBC-coupled NP before administering to prevent settling and aggregation of RBCs. In another embodiment, the method may employ a syringe that removes the RBCs from a patient's own blood and then reinjects after quick adsorption. The syringe may be pre-loaded with anti-coagulant (that reverses upon re-injection to patient; e.g. drug marketed as Eloquis®), or a leukoreduction filter. An intra-arterial catheter may be employed that uses ultrasound to scan for the presence of arterial plaque prior to intracarotid injection, preventing embolization of atheromatous plaques. Similarly, a device to allow intracarotid (or other arterial injection) with simultaneous closure of the injection hole can be employed in these methods.

In still a further aspect, the compositions and methods can also be employed for imaging, such as to map capillary structure or pathology, wherein the drug is an imaging reagent. In one embodiment, a method of imaging a mammalian organ comprises injecting intravenously or intraarterially in vivo or ex vivo a composition comprising a red blood cell (RBC) having non-toxically coupled thereto a nanoparticle having a low shear modulus or low Young's modulus of less than 10 MPa and containing an imaging drug, wherein said nanoparticles are transferred from the RBC-coupled flexible NP to the vascular bed of a target organ of the subject and release the imaging drug in the selected target organ or vascular tissue. In one embodiment, the low shear modulus is less than 1 MPa.

All scientific and technical terms used herein have their known and normal meaning to a person of skill in the fields of biology, biotechnology and molecular biology and by reference to published texts, which provide one skilled in the art with a general guide to many of the terms used in the present application. However, for clarity, certain terms are defined as provided herein.

The terms "a" or "an" refers to one or more, for example, "an assay" is understood to represent one or more assays. As such, the terms "a" (or "an"), "one or more," and "at least one" are used interchangeably herein.

The term "about" as used herein when referring to a measurable value such as an amount, a temporal duration, and the like, is meant to encompass variations of up to ±10% from the specified value; as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about."

Various embodiments in the specification are presented using "comprising" language, which is inclusive of other components or method steps. When "comprising" is used, it is to be understood that related embodiments include descriptions using the "consisting of" terminology, which excludes other components or method steps, and "consisting essentially of" terminology, which excludes any components or method steps that substantially change the nature of the embodiment or invention.

EXAMPLES

The following examples disclose specific embodiments of preparation of compositions of this invention, their characteristics and uses. These examples should be construed to encompass any and all variations that become evident as a result of the teaching provided herein.

Example 1

Methods and Materials

Animal and human study protocols. All animal studies were carried out in strict accordance with Guide for the Care and Use of Laboratory Animals as adopted by National Institute of Health and approved by University of Pennsylvania Institutional Animal Care and Use Committee (IACUC). All studies involving human subjects were approved by the University of Pennsylvania Institutional Review Board. Written informed consent from donors was obtained for the use of blood samples and blood samples were destroyed after the study. Names and personal information about individual participants were not taken. The ex vivo human lungs were donated from the local organ procurement agency, Gift of Life, after they had determined the lungs were not suitable for transplantation into a recipient, and therefore would have been disposed of if they were not used for our study.

Synthesis of and conjugation of proteins to NCs. The synthesis, characterization, radiolabeling, and fluorescent labeling of the NCs employed here have all previously been described, including liposomes[33], LDNGs[5], PLGA-PVA NCs, albumin NPs, and AAVs. Polystyrene NPs were purchased from Polysciences, Inc.

Blood Collection and Isolation of RBCs. Isolation of erythrocytes (RBCs) was performed via the methods previously described[34]. Briefly, whole blood from CJ7BL/6J mice was collected in EDTA; blood from rats and well as human voluntary donors was collected in ~3.2% Na citrate (BD Vacutainer). Blood from pigs were collected in in 1× CPDA-1 (Sigma). In addition, whole blood from CJ7BL/6J mice was collected in tubes without any anti-coagulants. Blood was then spun at 1000 g for 10 min at 4° C.; plasma and buffy coat were removed and discarded. Serum was stored at 4° C. for 3 h until use. Isolated RBCs were washed extensively with 1× Dulbecco's Phosphate Buffered Saline (DPBS), centrifuged (500 g, 15 min, 4° C.) and supernatant was discarded. This wash step was repeated for a total of 3 times.

Adsorption of NCs to RBCs. Briefly, RBCs were incubated with either unmodified or IgG-coated nanoparticles (NP) at a ratios between 200:1 and 3000:1 for 1 h under constant rotation at 4° C. in PBS or different % of serum (0%-100%). NP:RBC solution was washed with PBS three times at 100 g for 8 min to remove unattached NPs.

RBC Agglutination. Agglutination of RBCs were performed as previous reported[34]. Briefly, RBC and NP:RBC suspensions at 1% hematocrit was placed onto a U-shaped well plate at 37° C. for 1 h. In addition, RBC and NP:RBC suspensions were placed on a glass slide and observed using a Micromaster microscope (Fisher Scientific) equipped with micro-camera on a 25× objective lenses.

IV-injected NCs in mice. For all mouse experiments, we used C57BL/6 adult mice. Biodistribution of radiotraced NCs and fluorescence imaging of the lungs was performed as previously described[32,33]. For instillation of LPS, the mice were anesthetized with ketamine and xylazine, orotracheally intubated with a 20-gauge angiocatheter, and then LPS was instilled as at 1 mg/kg[33]. Pulmonary artery pressures were measured by putting the orotracheally intubated mouse on a ventilator, making a thoracotomy over the left anterior chest, and inserting a pressure sensor into the right ventricle.

IA-injected NCs in mice. The right main carotid artery was exposed and cannulated with a heparin coated catheter. The catheter was flushed with PBS immediately before and after NC injection. 30 minutes after injection, the catheter was flushed again, and the animal sacrificed.

IV-injected NCs in pigs. As previously described[37], 2-7-day-old Yorkshire pigs were anesthetized, endotracheally intubated, cannulated in the left internal jugular (for NC injection) and right femoral artery (for blood pressure and blood gas monitoring, and then injected IV with NCs, followed by radiotracer biodistribution measurement as for the mice.

Ex vivo human lung biodistribution. Human lungs were obtained after organ harvest from transplant donors whose lungs were in advance deemed unsuitable for transplantation due to radiographic evidence of alveolar filling and low $PaO_2$ to $FiO_2$ (P/F) ratios. The lungs were harvested by the organ procurement team and kept at 4° C. until the experiment, which was done within 12 hours of organ harvest. The lungs were first inflated with low pressure oxygen and the main bronchus clamped. Pulmonary artery subsegmental branches were endovascularly cannulated, and then sealed to the artery opening with with tissue glue composed of 30% bovine serum albumin (BSA) mixed at 1:1 with glutaraldehyde, thus preventing retrograde efflux of solutions injected into the artery branch. The pulmonary veins were also cannulated to aid with efflux of solutions that flowed through the lungs. The lungs were then perfused with 3% BSA in PBS at 25 cm $H_2O$ of pressure. We then injected into the artery, via its sealed catheter, $I^{125}$-labeled nanogels that were adsorbed onto human RBCs, and let ran 3% BSA-in-PBS through for 5 minutes. We then injected into the same artery $I^{131}$-labeled nanogels that were not adsorbed onto RBCs. We then ran 3% BSA-in-PBS through for 5 minutes. Finally, we injected a green tissue dye. The entire lung lobe was then dissected into 2 mL segments, which were analyzed for green dye intensity and measured in a gamma counter. We analyzed the green regions which were perfused by the chosen subsegmental artery separately, and the entire lobe collectively.

Example 2

Polystyrene Beads are Much Harder Than Liposomes and Nanogels

Quartz crystal microbalance measurements of shear modulus for polystyrene beads, lysozyme-dextran nanogels, and liposomes were performed. Experiments were performed with aqueous nanoparticle solutions (0.5 mg/mL) flowing over a complementary quartz surface (0.007 mL/minute).

Shear modulus values were obtained via application of the Voigt viscoelastic model1 to the third, fifth, and seventh harmonic outputs for adhered nanoparticle films. Liposomes exhibited a shear modulus of 202.137 kPa±125.648 kPa, nanogels a modulus of 67.878 kPa±24.799 kPa, and polystyrene beads a shear modulus of 8.472 MPa±2.398 MPa. Methods used are as described in Dun& G, Thormann E, Dedinaite A. Quartz Crystal Microbalance with Dissipation (QCM-D) studies of the viscoelastic response from a continuously growing grafted polyelectrolyte layer. J Colloid Interface Sci. 2013 Oct. 15; 408:229-34. The results of this example are shown in the graph of FIG. 1.

Tapping mode atomic force microscopy provided further confirmation of the softness of hydrogel nanoparticles. The morphology of lysozyme-dextran nanogels deposited on a surface with complementary chemistry was taken with tapping mode atomic force microscopy (AFM), and an AFM micrograph (data not shown) indicated the height of deposited nanogels in nm.

Direct application of a 22 nm radius probe to an agglutinated nanogel multilayer at 500 nm/sec provided stress-strain curves (data not shown). Direct deformation was shown by tip compression of the nanogel multilayer. Application of a Hertzian contact mechanics model to nine stress-strain curves indicated an average elastic modulus of 88 kPa for nanogel multilayers. See methods previously described[26].

Example 3

Soft Nanoparticles Have Much Greater End-Organ Delivery Than Hard Nanoparticles

Nanoparticles (NPs) including soft nanoparticles such as liposomes and hydrogels (also referred to as nanogels) and hard nanoparticles such as polystyrene were coated with IgG (covalently bound to the NP surface). These coated NPs were adsorbed onto mouse RBCs ex vivo, and injected intravenously into mice. Organ uptake was measured 30 minutes later using a gamma-counter to measure the I-125-labeled nanoparticles.

Figure 2:
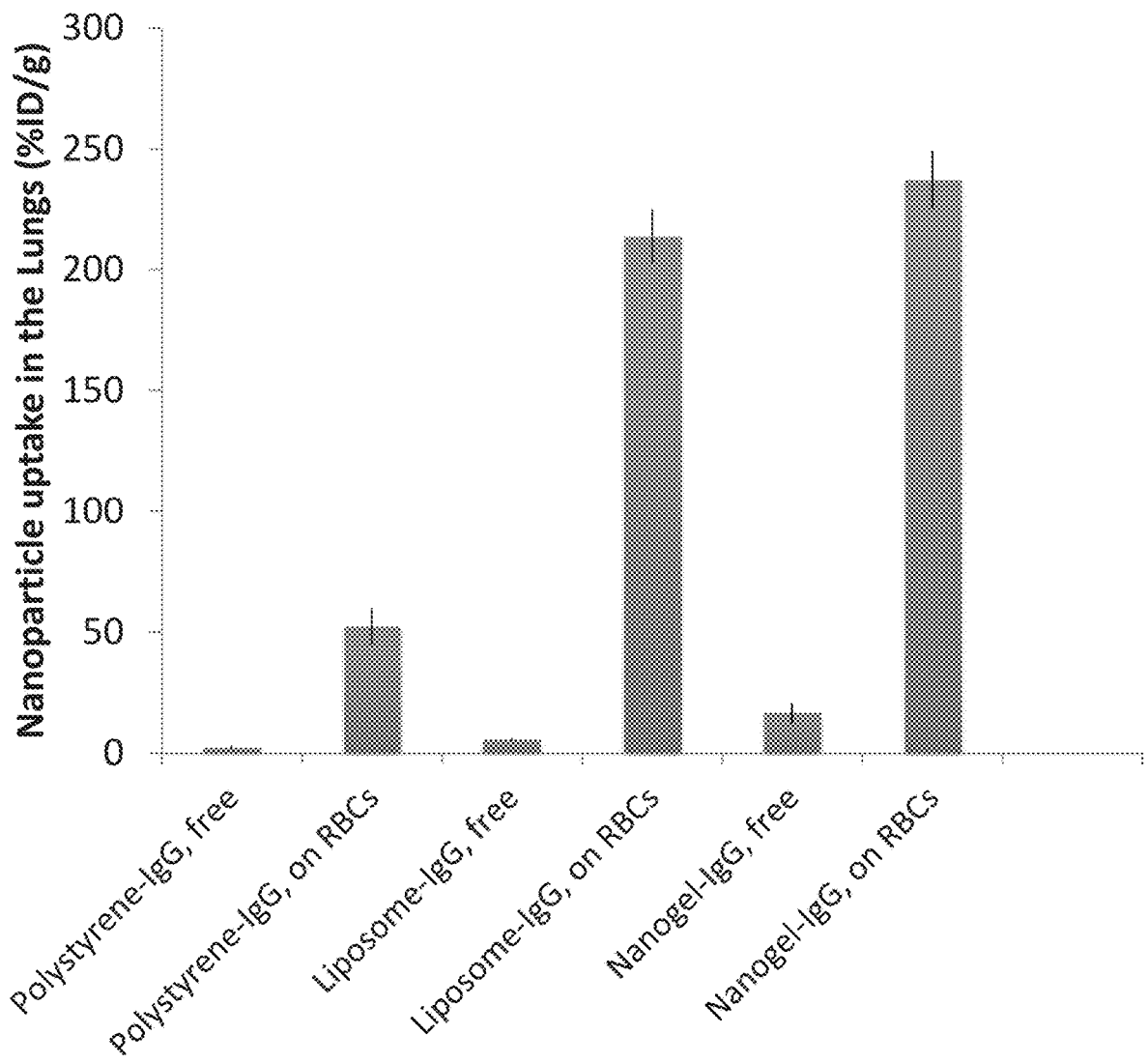
FIG. 2 is a graph showing that soft nanoparticles (e.g., liposomes, nanogels) have much greater end-organ delivery than hard nanoparticles (e.g., polystyrene). Nanoparticles (NPs) coated with IgG (covalently bound to the NP surface) were adsorbed onto mouse RBCs ex vivo, injected intravenously into mice, and then organ uptake was measured 30 minutes later using a gamma-counter to measure the I-125-labeled nanoparticles. As a control, free NPs (no RBC adsorption) are also shown. Plotted is lung accumulation of NPs as the % ID/g, which is the percentage of the injected dose found in the lungs, divided by the weight of the lungs in grams. Note that RBC-adsorption increases all NP uptake in the lungs, but the magnitude of uptake is much greater for soft NPs (liposomes & nanogels) than for hard NPs (polystyrene). Note that these injections were done intravenously, so the end-organ which accumulates the nanoparticles is the lungs, since the lungs are the first capillary bed met by agents injected intravenously.

The results are illustrated in FIG. 2. As a control, free NPs (no RBC adsorption) are also shown. The graph of FIG. 2 plotted lung accumulation of NPs as the % ID/g, which is the percentage of the injected dose found in the lungs, divided by the weight of the lungs in grams. RBC-adsorption increased all NP uptake in the lungs, but the magnitude of uptake is much greater for soft NPs (liposomes and nanogels) than for hard NPs (polystyrene).

Example 4

Protein on the Surface of NPs Increase Their Adsorption Onto RBCs

Protein as represented by IgG was covalently bound to the NPs (polystyrene, liposome and hydrogel) using previously described conjugation chemistries. In one example, the chemistry was the use of EDAC to bond IgG to polystyrene with carboxylate surface groups. The coated NPs and non-coated NP controls were then adsorbed onto RBCs, and the fraction of NPs that adsorbed was measured after 1 hr of adsorption, by tracing the I-125-labeled NPs. Note this same experiment was done with bovine serum albumin (BSA) coating the nanogels and obtained 35% RBC adsorption.

Figure 3:
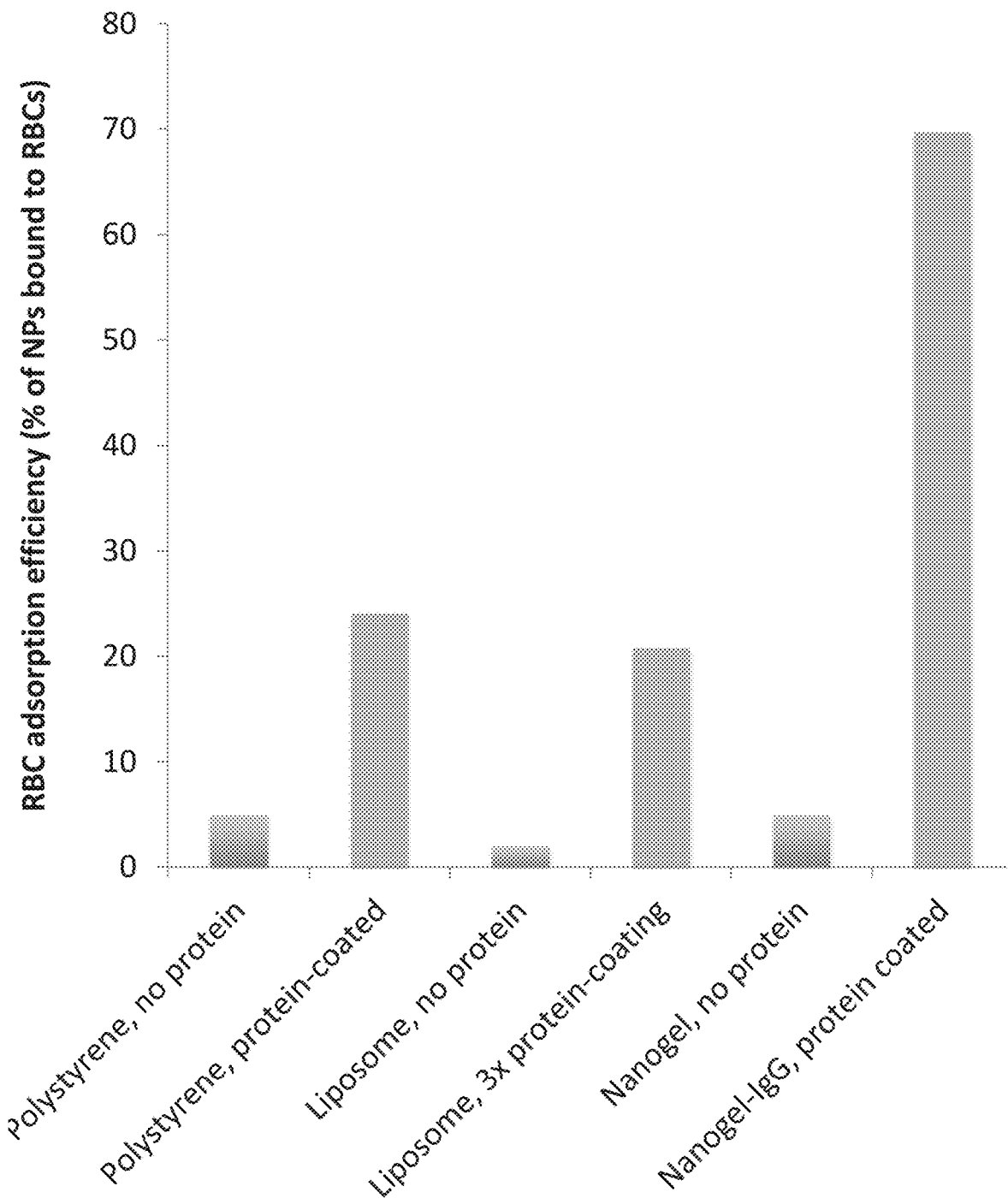
FIG. 3 is a graph showing that protein on the surface of NPs increases their adsorption onto RBCs. Protein (in this case IgG) was covalently bound to the NPs using previously described conjugation chemistries (e.g., EDAC to bond IgG to polystyrene with carboxylate surface groups). NPs were then adsorbed onto RBCs, and the fraction of NPs that adsorbed was measured after 1 hr of adsorption, by tracing the I-125-labeled NPs. Plotted is RBC adsorption efficiency in % of NPs bound to RBCs). This same experiment was done with bovine serum albumin (BSA) coating the nanogels and obtained 35% RBC adsorption.

The results of this experiment are shown in FIG. 3, indicating that the protein coating increases NP adsorption onto RBCs.

Example 5

Soft NPs are Less Toxic Than Hard NPs as Measured by Safety Hemolysis and Agglutination of RBCS Hemolytic curves for naïve RBC vs NP-adsorbed RBC compositions were obtained after immediate exposure to different concentrations of NaCl. Curves were determined for NP:RBC ratio (2000:1) of either polystyrene or hydrogel nanoparticles, compared to no nanoparticles. As demonstrated in FIG. 4, the compositions composed of hydrogel adsorbed to RBC (NG:RBC) were sensitive to hemolysis at a lower concentration of NaCl.

Example 6

Intra-Arterial Injection of RH NPs Leads to Delivery to the End-Organ Feed by that Artery Mice were injected with nanogels (NGs) adsorbed onto RBCs (or free NGs used as control), into the carotid artery. Uptake of the NGs was then measured by % ID per organ in blood, heart, lungs, liver, spleen, kidney, brain, face and thyroid.

Figure 5:
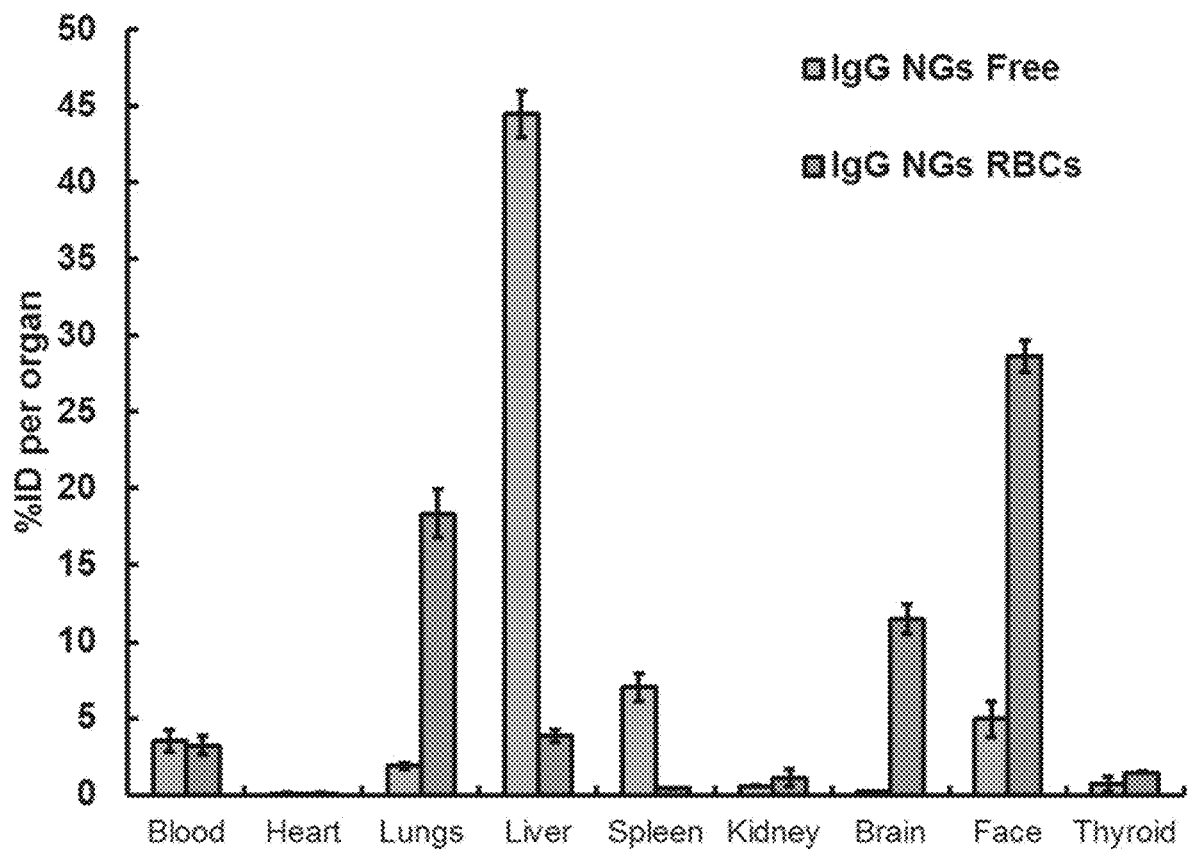
FIG. 5 is a graph showing that intra-arterial injection of RBC-hitchhiking (RH) NPs leads to delivery to the end-organ feed by that artery. Here, mice were injected with nanogels (NGs) adsorbed onto RBCs (right dark-grey column for each organ, or free NGs as control, left light-grey column for each organ), with the injection into the carotid artery. This led to very strong uptake in the brain as it distributed through the internal carotid and was transferred to the brain. Delivery also occurred to the face because the mouse's pterygopalletine artery also received delivery.

As illustrated in the bar graph of FIG. 5, very strong uptake was shown in the brain as it distributed through the internal carotid and was transferred to the brain cells. Delivery also occurred to the face because the mouse's pterygopalletine artery was where the carotid cathery was placed.

The typical manner in which a catheter would be inserted to achieve delivery of the compositions to the brain arteries after a stroke, such as immediately after endovascular embolectomy using a stent retriever device, is that used in such trials as the MR CLEAN study previously described[27].

Example 7

Hydrogel NPs for Drug Delivery to Lungs

Lysozyme-dextran nanogels were synthesized and functionalized with antibodies as described previously[2]. PE:PC liposomes were synthesized through standard extrusion techniques. Lysozyme-dextran nanogels and liposome hydrodynamic diameter was assessed via DLS. Polystyrene nanoparticles of similar size were purchased. Different quantities of nanoparticles were incubated with mouse RBCs at 10% hematocrit to accomplish physisorption, followed by centrifugation and washing to remove unbound nanoparticles from RBCs pellets. Efficiency of nanoparticles coupling to RBCs was evaluated through quantification of $^{125}$I label on nanoparticles.

Following nanoparticles physisorption, RBC hemolysis in response to osmotic, mechanical, and oxidative stress was evaluated through optical absorbance. RBC agglutination was evaluated in sedimentation assays and RBC smears. Polystyrene nanoparticles and lysozyme-dextran nanogels were imaged on RBCs with scanning electron microscopy. RBCs ($^{51}$Cr tracer) bearing lysozyme-dextran nanogels or polystyrene nanoparticles ($^{125}$I tracer) were injected intravenously in mice and allowed to circulate for 30 minutes.

Polystyrene nanoparticles adsorb onto RBCs at higher efficiency than lysozyme-dextran nanogels, while liposomes manifest minimal physisorption on RBCs. SEM images confirmed physisorption of lysozyme-dextran nanogels and polystyrene nanoparticles on RBCs (data not shown). However, polystyrene nanoparticles result in concentration-dependent agglutination of RBCs, while lysozyme-dextran nanogels do not cause RBC agglutination up to loading of 2000 lysozyme-dextran nanogels per RBC (data not shown).

Figure 4:
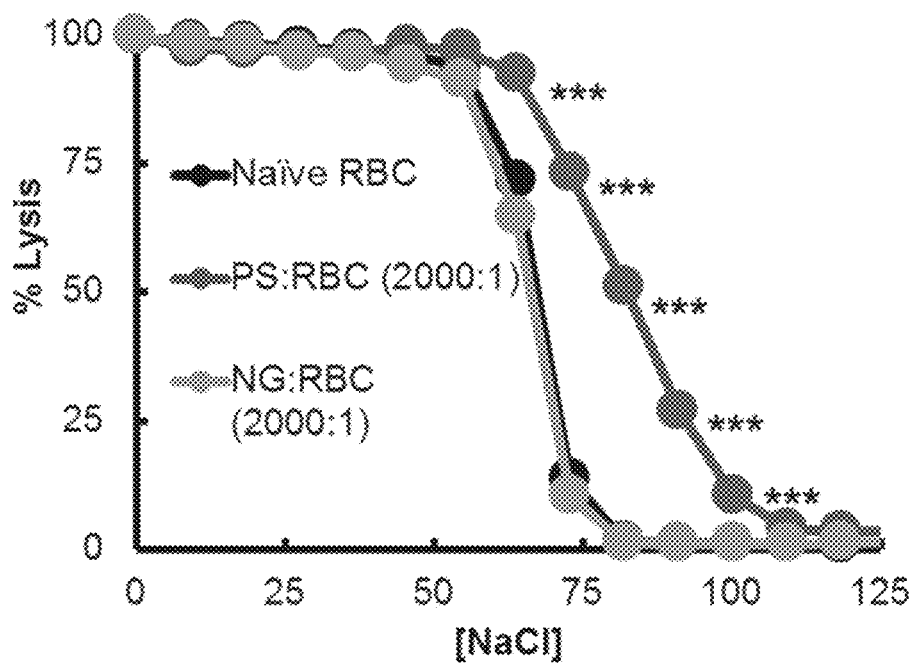
FIG. 4 is a graph showing that soft NPs are less toxic than hard NPs in terms of safety hemolysis and agglutination of RBCs. Osmotic fragility of RBCs (naïve or with NPs adsorbed onto their surface) are shown in curves. Hemolytic curves for RBC/NP:RBC were obtained after immediate exposure to different NaCl concentrations [NaCl]. Curves were determined for NP:RBC ratio (2000:1) of either PS (polystyrene, dark grey) or NG (nanogel, light grey), compared to no NPs (black).
Figure 6:
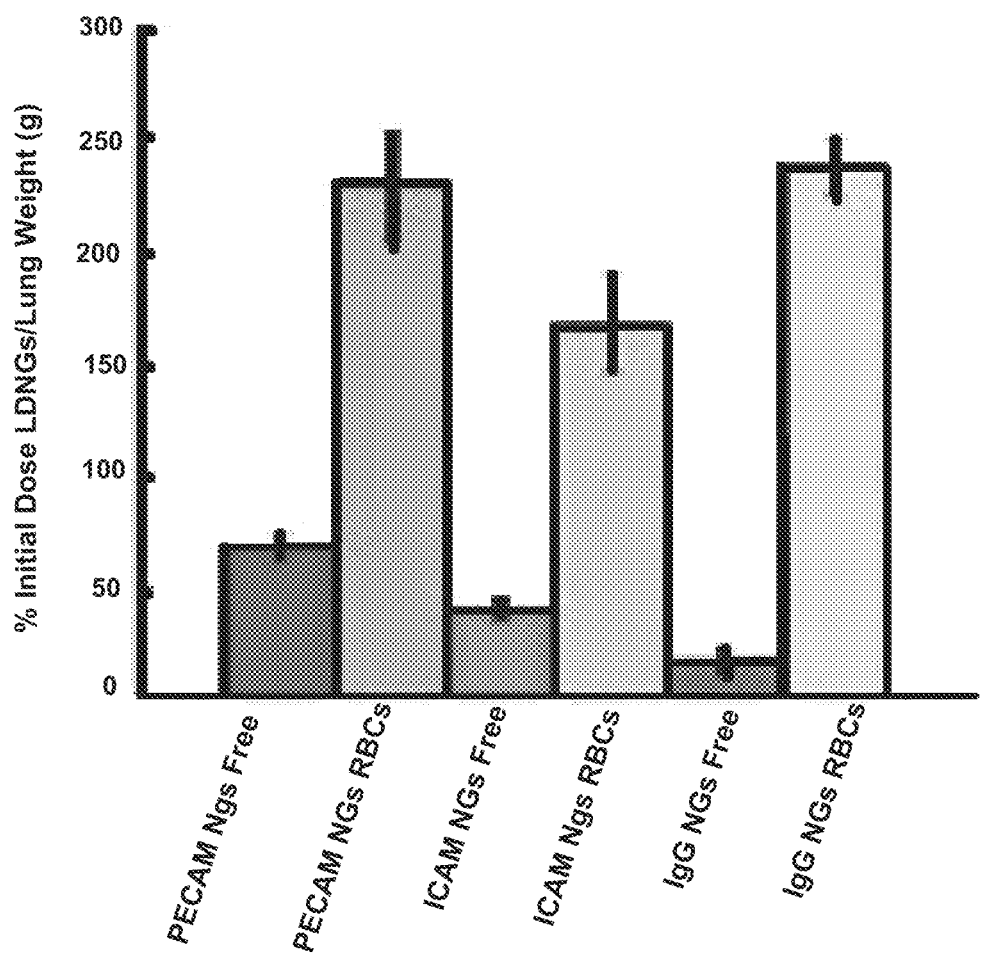
FIG. 6 is a bar graph showing the lung distribution of lysozyme-dextran nanogels adsorbed on RBCs.
Figure 7:
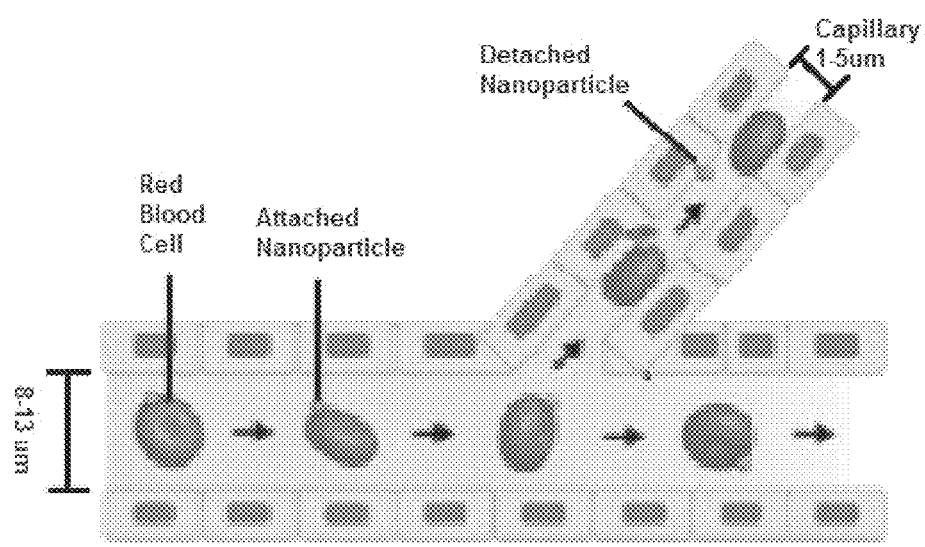
FIG. 7 is a schematic showing RBC-NP delivery and capillary squeezing. The NP are retained on the RBC surface until the RBC-NP complex squeezes into capillaries, and there the transfer of NPs occurs, at the capillary bed. Additional mechanisms may also contribute to transfers of the NPs and thus the drug to various cells at the selected site.

Polystyrene nanoparticles loading greater than 200 nanoparticles:1 RBC sensitized RBCs to osmotic, mechanical, and oxidative stresses, but lysozyme-dextran nanogels, up to 2000 lysozyme-dextran nanogels:1 RBC, did not alter RBC sensitivity (FIG. 4). Applied in vivo, RBCs successfully delivered lysozyme-dextran nanogels to the lungs (FIG. 6). Whereas free lysozyme-dextran nanogels exhibited enhanced adhesion in the lungs with the addition of antibodies targeting PECAM or ICAM, lysozyme-dextran nanogels loaded on RBCs more efficiently deposited in the lungs, regardless of lysozyme-dextran nanogels affinity. ~30% of initially injected RBC-loaded lysozyme-dextran nanogels remained in the lungs after 30 m, while $^{51}$Cr tracing indicated that injected carrier RBCs did not adhere in the lungs and pulmonary pressure measurements indicated no formation of lung emboli due to lysozyme-dextran nanogels adhesion or RBC agglutination.

This data demonstrated that lysozyme-dextran nanogels can reversibly adsorb on RBCs, allowing superior affinity-independent RBC-mediated delivery of a nanoparticle to the lung capillaries, while bypassing RBC sensitizing observed for other nanoparticles.

Figure 8:
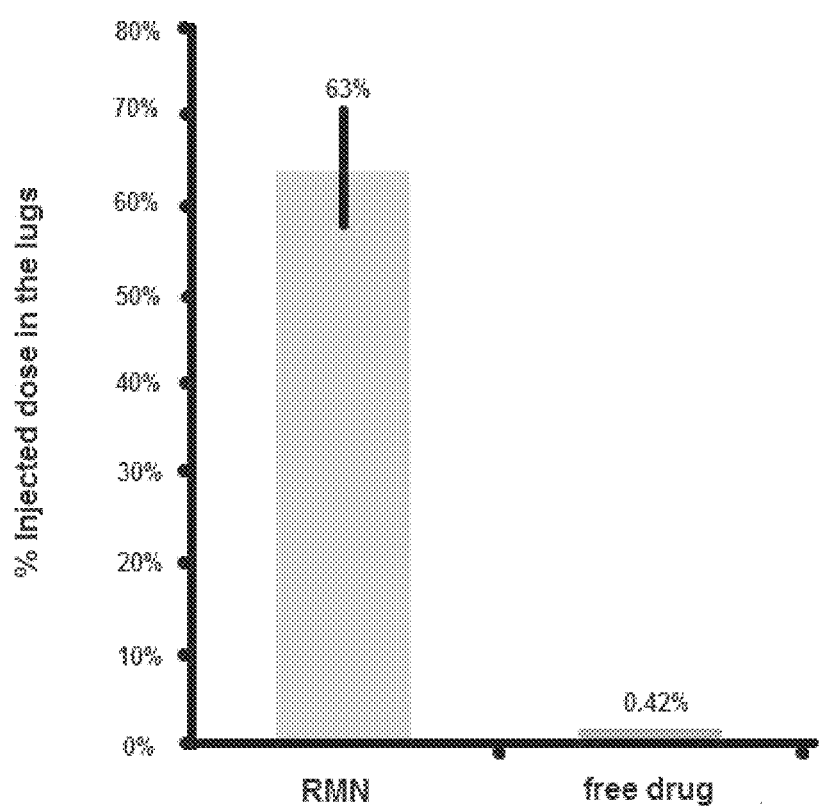
FIG. 8 is a bar graph showing % injected dose of the drug delivered to the lungs via a composition as described herein (also referred to as a RBC-hitchhiking Multi-drug-loaded Nanogel, i.e., an RMN) vs. the administration of free drug.
Figure 9:
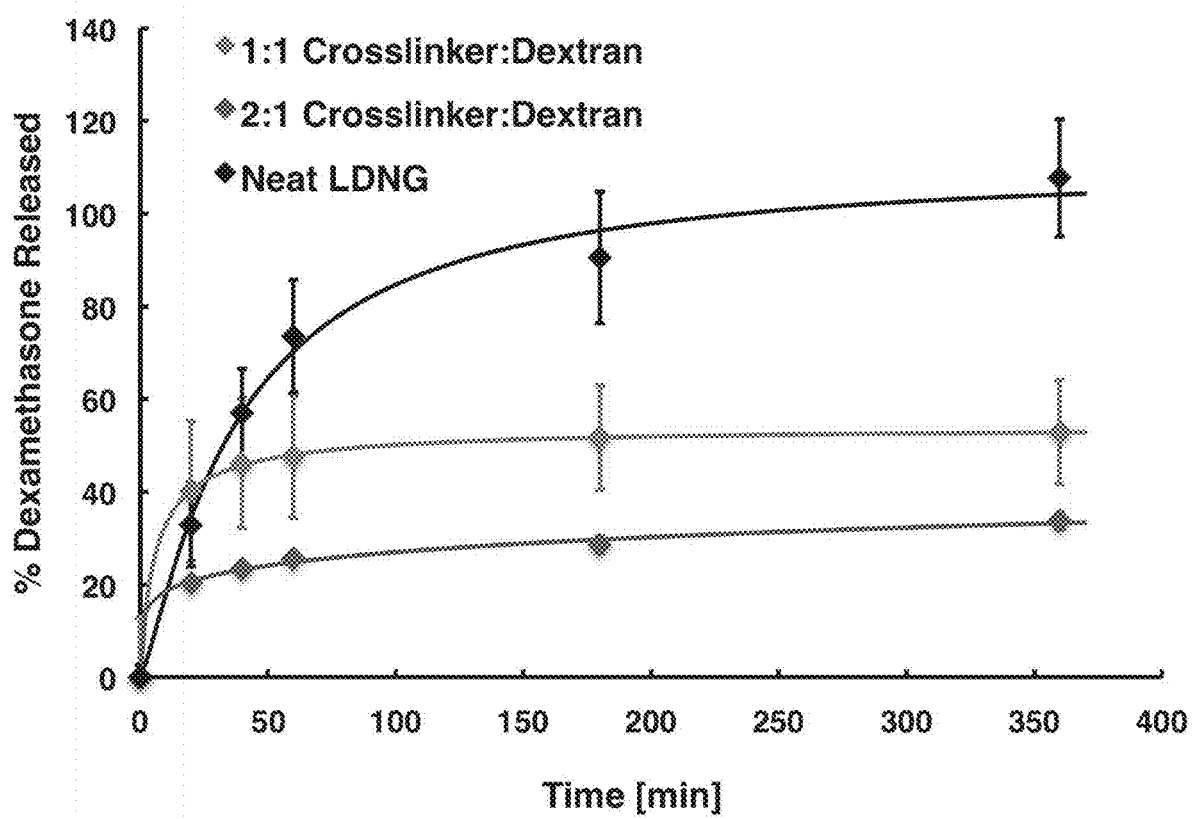
FIG. 9 shows curves generated by plotting % dexamethasone released over time for a 1:1 or 2:1 crosslinked dextran NP or by neat lysozyme dextran nanogel (LDNG).

For use in treating the lung disease, ARDs, for example, this drug delivery system employs multi-drug-loaded flexible nanoparticles, exemplified as nanogels, about 300-nanometer globular hydrogels formed from controlled reaction of protein with dextran. The nanogels are loaded with multiple FDA approved drugs, such as dexamethasone and albuterol, which are known to ameliorate ARDS but have off-target dose-limiting side effects when delivered without lung-targeting. In order to deliver the multi-drug-loaded nanogels to the lungs, we harvest red blood cells via a simple low-volume blood draw, and then physisorb the nanogels onto the RBC surface. When the nanogel-RBCs are injected back into the veins, the first capillary bed they reach is the pulmonary alveolar capillaries. The compositions described herein deliver at least 60% of the injected dose to endothelial cells in the lungs, compared to ~0.4% for typical free drugs (not in nanoparticles). See FIG. 8. By concentrating drugs more than 150-fold in the lungs, these compositions eliminate the off-target side effects of delivered drugs, solving a significant pharmacological problem in the treatment of ARDS. Since these compositions can shuttle multiple drugs, they can target multiple pathways and thus multiple subtypes of ARDS, solving the problem of heterogeneity of infection.

We are now loading the nanogels with 3 different small molecule drugs which are already FDA approved for other indications. Each drug has been shown to ameliorate ARDS, but increased mortality because, when delivered without drug carriers, most of the dose goes to organs other than the lungs and causes severe side effects. By concentrating these drugs in the lungs, our compositions should dramatically improve the odds of ameliorating ARDS.

Importantly, the compositions and methods of use described herein is a platform technology that will be applied to other diseases. Our initial target is a lung disease because the capillary bed in the lungs is the first encountered by compositions described herein after intravenous injection. However, using standard intra-arterial catheters, we can also inject these compositions directly into any organ to achieve very high delivery to the target organ. Therefore, we use intra-arterial catheters to inject the compositions comprising RBC coupled with flexible NPs carrying drugs into the carotid to treat ischemic stroke, into the coronary arteries after myocardial infarction (heart attack), and into various arteries before transplanting organs into recipient patients. All three of these latter applications are examples of ischemia-reperfusion injuries (IRIs) and thus will likely benefit from the concentration of drugs carried by our compositions that only improve IRI at very high concentrations.

Example 8

Nanocarrier Formulation Strongly Affects Performance in RBC-Hitchhiking

We previously attempted an early version of RBC-hitchhiking (RH): NCs were mixed with RBCs ex vivo, causing the NCs to adsorb onto the RBCs[4]. The NCs were then injected intravenously (IV), and were serendipitously found to accumulate somewhat in the lungs. The hypothesized mechanism was that when the RBCs squeeze through the lung capillaries they transferred the NCs to the pulmonary capillary endothelial cells. While the basic idea of cell-hitchhiking, and RBC-hitchhiking (RH) in particular, was sound, the practical results were not impressive. In those early RH experiments, NCs only achieved 3% ID in the lungs and a lung-to-liver concentration ratio of 1[4]. Compare that to a common lung-targeting affinity-moiety, anti-PECAM antibodies, which gave 30% ID in the lung and a lung-to-liver ratio of 10[32,33]. More importantly, the NPs in our early RH studies caused extensive, dose-limiting toxicities on the RBCs themselves[34].

To overcome the above challenges, we explored the idea of combining cell-based therapies with NCs. Here we have optimized, generalized, and extended our early concept of RH, producing a much more effective and broadly applicable platform technology. Our goals were to move RH towards being a clinically useful platform technology by: finding the optimal NC properties for RH, determining the mechanism of RH, determining if RH works in large animals and humans, and evaluating the safety of optimized RH. Perhaps more importantly, we sought to extend RH to not just target the lung, but any organ. In particular, we hypothesized that while IV-injected RH-NCs would accumulate in the lungs (the first capillary bed downstream of an IV injection), intra-arterially (IA) injected RH-NCs would accumulate in the immediately downstream organ. Such IA delivery of RH-NCs could treat two of the leading causes of cardiovascular death: heart attack and stroke. For severe heart attacks and stroke, it is standard of care to insert a catheter into the affected artery to remove flow obstructions, which helps, but still has poor patient outcomes. Therefore, we sought to determine if RH could be injected intra-arterially (IA), as an IA catheter would already be in place during heart attack and stroke treatment. This extension of RH can show the synergy between combining nanomedicine with different size-scale technologies, here the synergistic combination of "nano-micro-macro": nano-scale drug carriers+micro-scale RBCs+macro-scale IA catheters.

Figure 10A:
FIG. 10A is a scanning electron micrograph (SEM) showing that clinically translatable nanocarriers adsorb onto red blood cells. NCs were mixed with RBCs in vitro, leading to adsorption of NCs onto RBCs. The SEM shows PS NP and nanogels attached to the surface of murine RBCs.
Figure 10B:
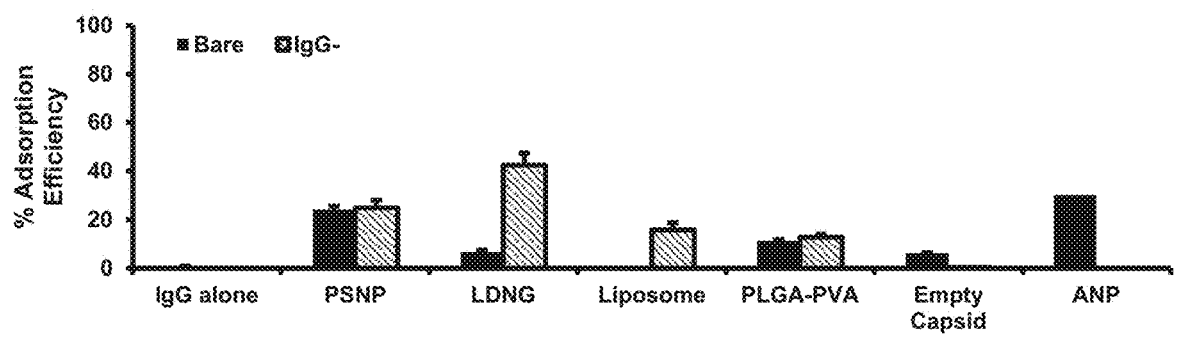
FIG. 10B is a graph showing adsorption efficiencies of radiolabeled NCs onto RBCs, as defined by the % of total NC added to RBCs that pellet with RBCs.
Figure 10C:
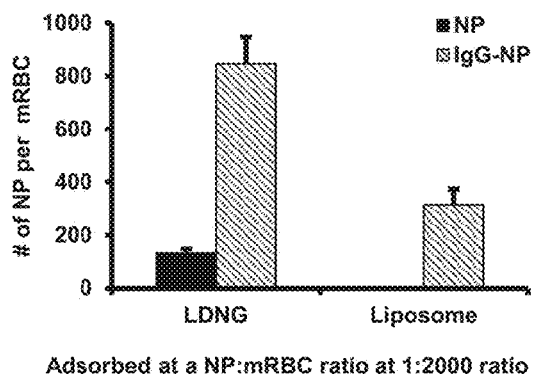
FIG. 10C is a graph showing a number of nanoparticles (NPs) adsorbed per RBC, when NPs were mixed with RBCs at ratio of 2000 NPs per murine RBC (mRBC).
Figure 10D:
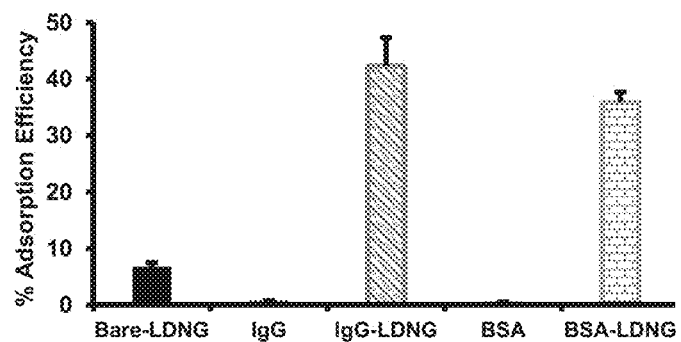
FIG. 10D is a graph showing adsorption efficiencies onto RBCs of free proteins (IgG and BSA) compared to free nanogels (Bare-LDNG) and to nanogels coated with each protein (IgG-LDNG and BSA-LDNG).

We began by finding optimal formulations and conditions for NC adsorption onto RBCs. RBCs were isolated from mice by venous blood draw, washed in buffer to remove serum, mixed with NCs and then incubated for 5 to 60 minutes, washed, and then analyzed for NP-to-RBC adsorption. FIG. 10A shows an electron micrograph of adsorbed NPs on RBCs. FIG. 10B shows the adsorption efficiency of a broad range of particles onto the RBCs. Notably, free IgG molecules do not show any adsorption, while all tested clinically-relevant nanoparticles do show adsorption, as does the 25-nanometer gene therapy vector adeno-associated virus (AAV). Also notable for RH optimization is that the two lowest-shear-modulus NPs, nanogels and liposomes, show a marked increase in adsorption efficiency when they are surface-coated with protein (here the protein is random IgG; FIGS. 10B and 10C). Furthermore, the identity of the protein coating the surface does not appear to be a major factor in adsorption (FIG. 10D).

Figure 10E:
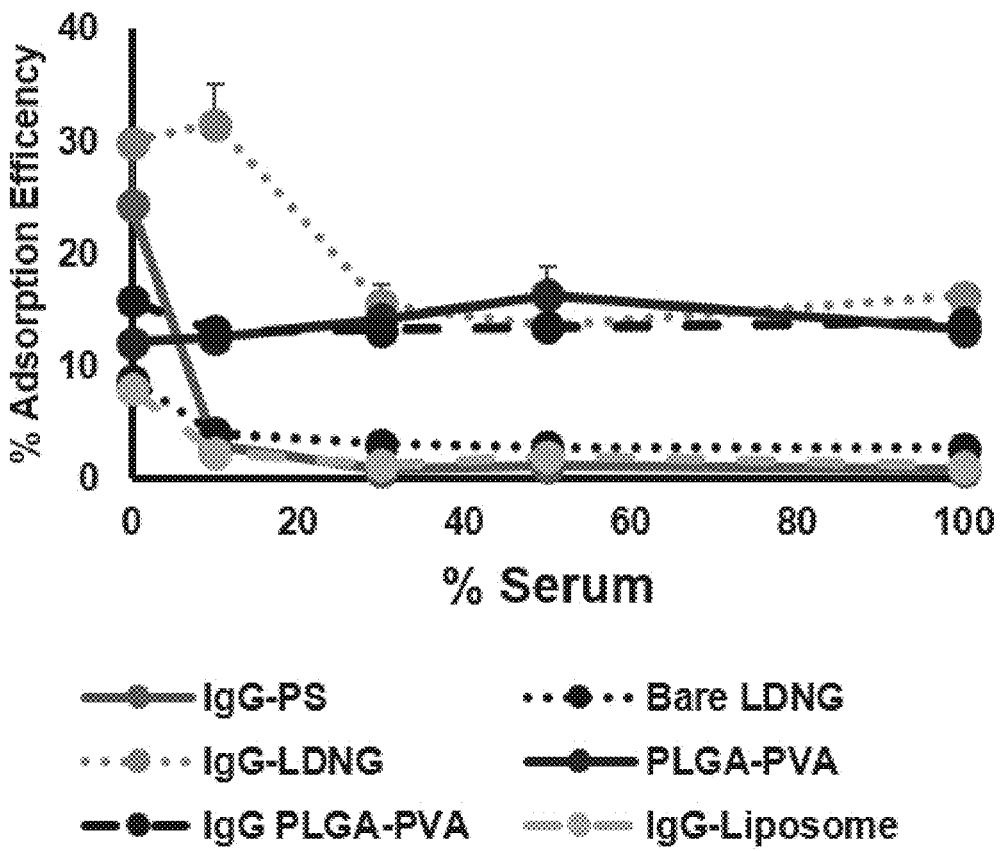
FIG. 10E is a graph showing adsorption efficiencies of unmodified and IgG-coated NCs with increasing concentrations of serum present in the buffer during adsorption.

In addition to the NC formulation, another major property affecting adsorption is the presence of residual serum in the buffer during adsorption. As seen in FIG. 10E, the presence of increasing serum causes complete loss of NC-to-RBC adsorption in some NCs (e.g., liposomes), while in other NCs there is no effect on adsorption (e.g., PLGA), or a plateau effect. By way of comparison to the clinical realm, typical packed red blood cell units (PRBCs) used clinically have 10% residual serum, while "washed" PRBCs have <<10%. These results indicate the importance of serum-free conditions to optimized RH.

Figure 11A:
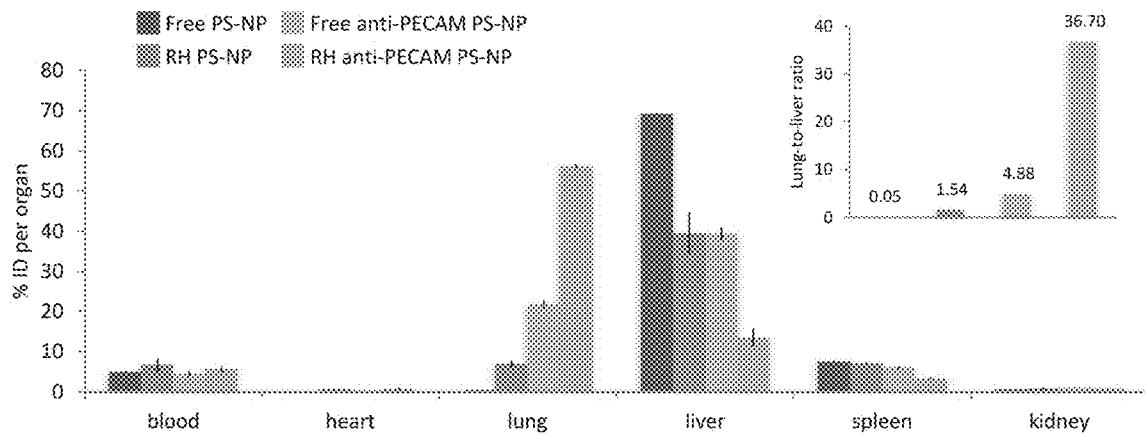
FIG. 11A shows that intravenous injection of optimized RBC-hitchhiking (RH) nanocarriers massively augments lung delivery without the need for an affinity moiety. Mice were injected IV with polystyrene nanoparticles (PSNPs) that were covalently coated with either IgG (dark leftmost bar in each organ set and insert is free PSNP, medium dark bar second from left in each organ set and insert is RH PSNP) or anti-PECAM antibodies (light grey bar third from left in each organ set and insert is free anti-PECAM PS-NP; RH anti-PECAM PS-NP is the light-grey rightmost bar in each organ set and insert) and radiolabled with I-125. Separate mice were injected with one of those two PSNPs adsorbed onto RBCs. Mice were sacrificed 30 minutes later and organs were measured in a gamma counter. Displayed is the percent injected dose (% ID) for each organ. Inset: lung-to-liver ratios, which are calculated by dividing the lung's % ID per gram of tissue (% ID/g) by the liver's % ID/g.

After optimizing NP-to-RBC adsorption, we next tested the efficacy of RH delivery to a target organ to find the best NCs for RH. As seen in FIG. 11A, when injected IV, polystyrene-NPs (PSNPs) covalently-coated with random IgG do not accumulate significantly in the lungs, but RH increases lung uptake 18-fold and the lung-to-liver ratio 32-fold. Additionally, RH can augment lung uptake of PSNPs coated with an affinity moiety. We tested PSNPs coated with anti-PECAM-monoclonal antibodies, as such targeting epitopes lead to higher lung uptake of this type of nanoparticle than any other affinity moiety published to date. RH increased lung-uptake 2.6-fold and the lung-to-liver ratio 7.5-fold. The combination of affinity-moiety plus RH thus increased the lung-to-liver ratio 760-fold (FIG. 11A inset). Thus, RH can augment delivery of both untargeted NCs and those that already have lung binding due to affinity moieties, with multiplicative effects when RH is combined with affinity moieties.

Figure 11B:
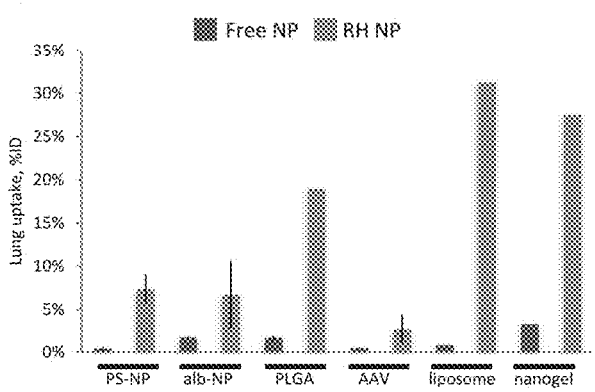
FIG. 11B is a bar graph showing % ID in the lung of NCs injected with the protocol described in FIG. 11A. The left bar in each NC set is Free NP while the right bar is RH NP.
Figure 11C:
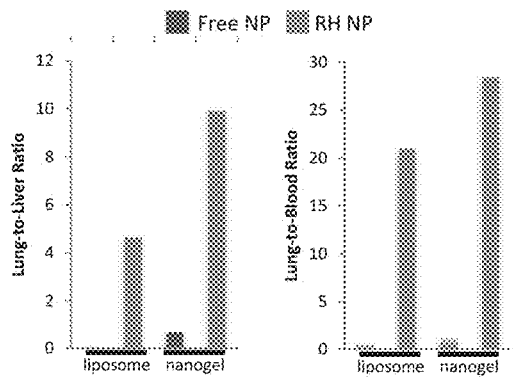
FIG. 11C shows two graphs: Lung-to-liver (left panel) and lung-to-blood (right panel) ratios of liposomes and nanogels, the two top performing NCs. The left bar in each NC set is Free NP while the right bar is RH NP.
Figure 11D:
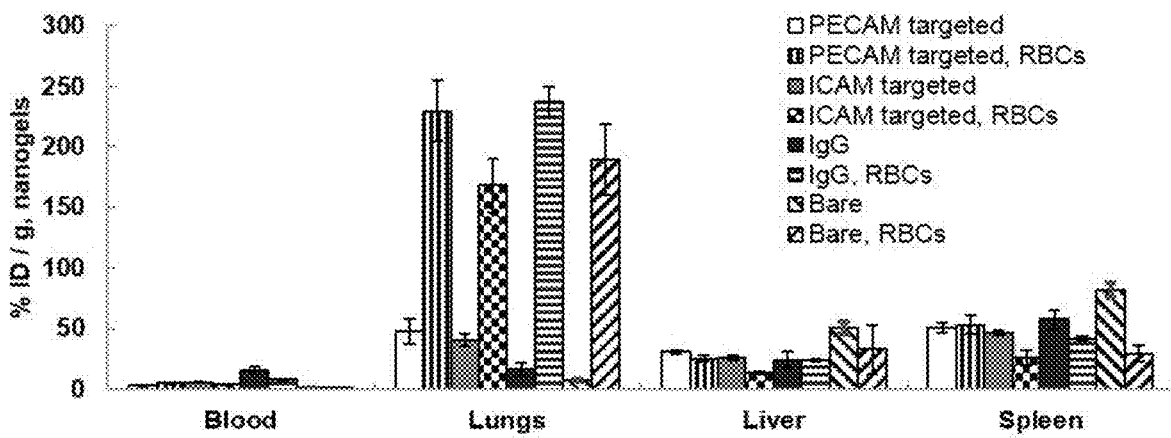
FIG. 11D is a bar graph showing that mice that were injected with nanogels that were either uncoated (bare) or covalently coated with 3 different antibodies (random IgG, anti-PECAM, or anti-ICAM). Other mice were injected with each of those 4 nanogel formats adsorbed onto RBCs. Plotted is % ID/g.

We next screened a variety of nanoparticles for their effectiveness in RH. When injected IV, RH augmented lung uptake in the case of every NC tested (FIG. 11B-11D). The fold-improvement of lung uptake provided by RH over free NCs ranged from 4- to 39-fold, with the NCs with the lowest-shear-modulus, liposomes and nanogels, having the highest values. Two key variables for determining a targeting modality effectiveness in organ targeting are the fold-improvement conferred by targeting on the target-organ-to-liver and target-organ-to-blood ratios, which for liposomes were 116× and 49×, respectively, with nanogels displaying similar values of 15× and 27× (FIG. 11C).

For these high-performing NCs, we next tested how RH interacts with concomitant affinity moieties. Like with PSNP, RH improves lung targeting of nanogels coated with affinity moieties such as anti-PECAM and anti-ICAM (FIG. 11D). Surprisingly, in RH, nanogels do not require affinity moieties to achieve their maximal binding: lung uptake was equally high whether the nanogels were covered in affinity moieties, random-IgG, or no surface coating at all. Thus, RH nanogels can achieve very high uptake without the use of affinity moieties. Indeed, with no affinity moieties, RH nanogels produce a lung-to-liver ratio 6.4-fold higher than that of anti-PECAM-nanogels, the best known targeting moiety for this size nanoparticle.

Example 9

RBC-Hitchhiking NCs are Taken up Into Cells Lining the Capillary Lumen of Target Organs The hypothesized mechanism underlying RH was originally that NCs on RBCs are transferred to the capillary endothelium as the RBCs squeeze through the pulmonary capillaries. However, previously, there was no data proving what cell type took up RH NCs, or even that the NCs were inside cells at all.

In one experiment, we used injected RH fluorescently-labeled nanogels IV, and sectioned the lungs for confocal imaging (images not shown). Mice were IV injected with RH rhodamine-conjugated nanogels, sacrificed 30 minutes later, and then the lungs were fixed and sectioned. The sections were stained for an endothelial marker (VE-cadherin), a leukocyte marker (NIMP,) and the rhodamine-nanogels fluoresced red. In the photographs of the gels (data not shown), NGs are seen to localize to the capillary endothelial cells, with not much of the nanogels going to the rare leukocytes. Nanogels do indeed appear to be inside endothelial cells (VE-cadherin+) and not present in the lumens of large blood vessels, confirming the original hypothesized mechanism.

We next determined if this same RH mechanism is present in lungs suffering from a pathology that would be a clinically realistic target for RH-based therapies. We focused on the inflammatory disease ARDS (acute respiratory distress syndrome), which causes pulmonary capillary endothelial dysfunction, influx of destructive leukocytes, and has been identified as a key target for pulmonary nanomedicine[3]. We used a well-validated mouse model of ARDS, lipopolysaccharide (LPS) instillation into the lungs. In this experiment, mice were given intratracheal LPS to model the disease ARDS and then RH NCs were injected as described immediately above. A 10× image and a 40× magnification of the region marker V were taken (data not shown). Red nanogels were present in an overlapping distribution with both endothelial cells and leukocytes. Images of another region of the tissue, displayed only 2 markers each (data not shown). As in naive mice, NCs were taken up into pulmonary capillary endothelial cells. Surprisingly, however, the NCs were also taken up by intravascular resident leukocytes, which reside in the capillary lumen during ARDS and have been implicated in ARDS pathology[35,36]. Thus, RH delivers NCs to multiple different cell types that line the capillary luminal surface.

Figure 12:
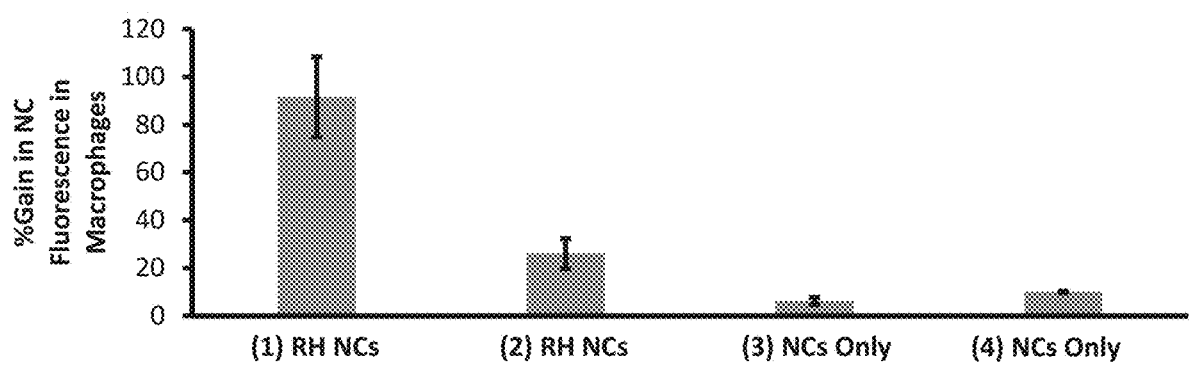
FIG. 12 is a bar graph quantifying macrophages' gain in nanogel-related fluorescence during each of the following experiments. RBC-hitchhiking NCs are taken up by endothelial cells and leukocytes lining the capillary lumen of target organs. Macrophages were plated in flow chambers and nanogels were flowed in either free or adsorbed onto RBCs. 4 separate experiments were conducted, with the first two being RH nanogels and the second two being free nanogels (data not shown). In the RH nanogels, the RH NGs localize to the macrophages, and the RBCs transiently localize with the macrophages (data not shown). In the free nanogels, very little nanogel signal localizes with the macrophages.

Having found that intravascular resident leukocytes strongly take up RH NCs, we next attempted to directly observe in real time transfer of NCs from RBCs to these leukocytes. Intravascular resident leukocytes in ARDS include both pulmonary intravascular macrophages (PIMs) and marginated neutrophils. To simulate PIMs, we seeded activated mouse macrophages onto the lumen surface of microfluidic chambers and flowed over them RH nanogels. Activated macrophages grabbed NC-coated RBCs and separate off the NCs, and then retained the NCs. See, e.g., FIG. 12.

Example 10

RBC-Hitchhiking Works Safely in Multiple Species and Multiple Target Organs

Figure 13A:
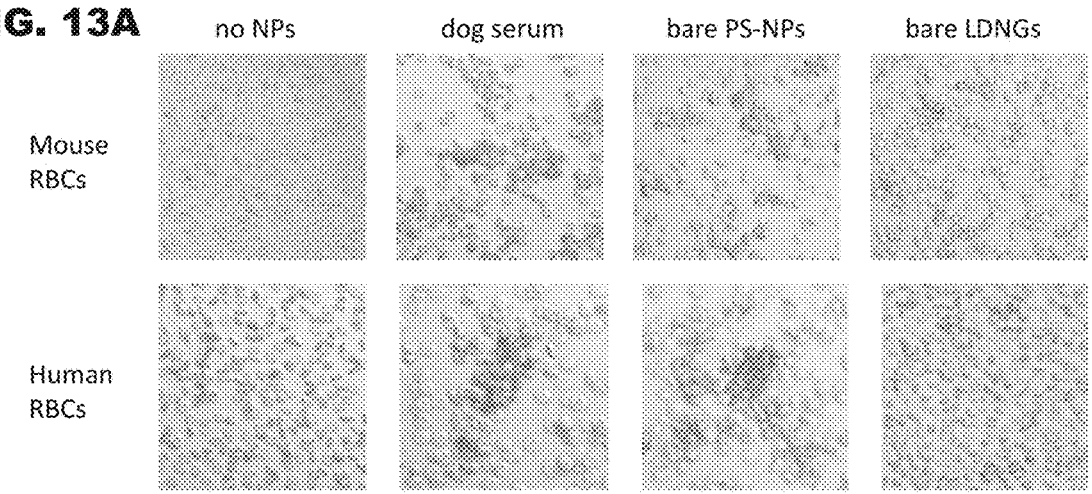
FIG. 13A shows that optimized NCs do not cause toxicity during RBC-hitchhiking. Mouse and human RBCs were mixed either with an agglutinating cross-species serum (dog serum) or NCs and then prepared as a "thin smear" slide. Dog serum causes RBCs to aggregate, as do bare PSNPs, but not nanogels.
Figure 13B:
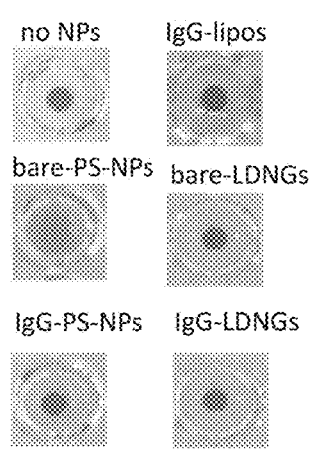
FIG. 13B shows a round-bottom well assay of RBC aggregation, in which aggregated RBCs form a diffuse haze while non-aggregated RBCs for a tight dark dot.

Having optimized RH formulation and determined the basic mechanism, we next endeavored to validate the safety of RH. We began by checking if the first step of RH, ex vivo adsorption of NCs onto RBCs, causes aggregation of RBCs (clinically called agglutination). RBC aggregation can be very toxic because it can cause pulmonary emboli, meaning RBC aggregates lodged in the pulmonary arteries. We first assayed RBC aggregation with the clinical protocol of "thin-smear" preparations (FIGS. 13A-13F). Uncoated PSNPs, the original NC used in early RH studies, causes severe RBC aggregation, on par with that caused by cross-species serum. However, clinically translatable NCs, such as nanogels, do not cause significant agglutination. To quantify the degree of RBC aggregation, we used the clinical gold standard, the round-bottom-well assay, in which non-aggregated RBCs settle into a tight dot at the bottom of the well, while aggregated RBCs form a lawn that appears as a diffuse haze (FIG. 13B). As with thin smears, uncoated PSNPs cause RBC agglutination at the maximum quantifiable by the assay. By contrast, no RBC agglutination is detectable for RBCs adsorbed with any of: PSNPs covalently coated with protein (as used in FIGS. 11A-11D), nanogels (+/– IgG coating), or liposomes. Thus, while some NCs (bare PSNPs) do cause severe RBC agglutination, most clinically relevant NCs do not cause significant RBC aggregation.

Figure 13C:
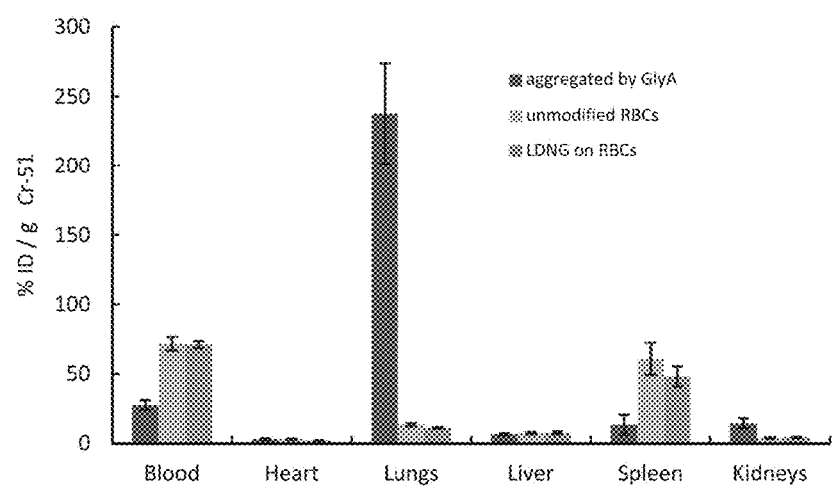
FIG. 13C is a graph showing the results of an experiment in which RH nanogels were prepared as done in FIG. 11A-11D, with the RBCs labeled with Cr51, and injected into mice, followed by sacrifice 30 minutes later and organ measurement on a gamma counter (unmodified RBC, middle bar in each organ set; LDNG on RBCs, right bar in each organ set). As a positive control, RBCs were intentionally aggregated with the GlyA antibody (left bar in each organ set).
Figure 13D:
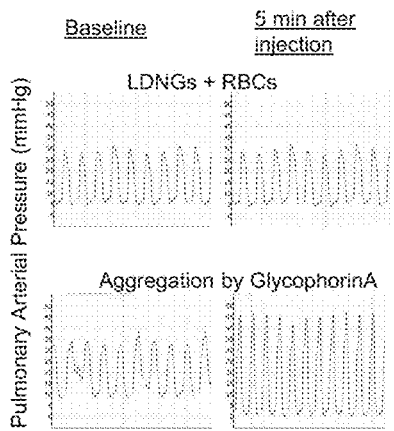
FIG. 13D is a set of 4 graphs showing pulmonary arterial pressure. RH nanogels and GlyA-aggregated antibodies were prepared as in FIG. 13C, but before sacrifice, the pulmonary artery pressure (PAP) was measured. 5 minutes after injection, GlyA (positive control) had increased the PAP, while RH nanogels did not.
Figure 13E:
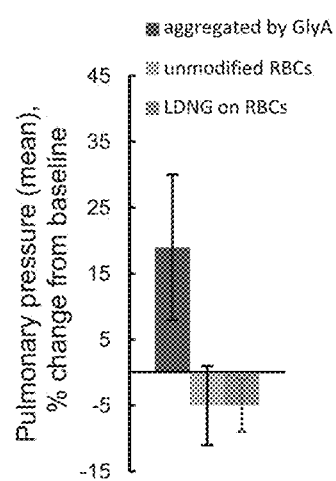
FIG. 13E is a graph showing quantification of the data of FIG. 13D. GlyA, left bar in each organ set; unmodified RBC, middle bar in each organ set; LDNG on RBCs, right bar in each organ set.
Figure 13F:
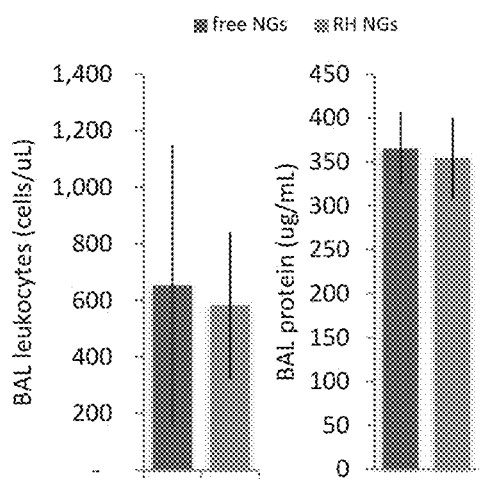
FIG. 13F shows the results of injecting mice with RH (right bar in each set) or free nanogels (left bar in each set) and intratracheally instilling same with LPS, followed by measurement of the bronchoalveolar lavage (BAL) levels of leukocytes (left graph) and protein (right graph), both measures of lung inflammation and ARDS.

We next tested whether RH causes RBCs to lodge in the target organ. Such clogging of vasculature could impede perfusion to the target organ, and in the case of lodging in the lung, cause increased pulmonary arterial pressures and subsequent right heart failure. To assay this, we labeled RBCs with Cr-51, injected them IV (with the RH target organ being the lungs) and measured their biodistribution. As a positive control, we intentionally aggregated RBCs with anti-glycophorin-A antibodies (GlyA). As seen in FIG. 13C, the positive control (GlyA) causes the RBCs to massively accumulate in the lungs. By contrast, RH NCs do not change lung uptake or blood levels at all compared to the negative control (IV-injected RBCs that have not been adsorbed to NCs).

Having shown RBCs do not remain in the target organ (lungs), we next checked that they do not lead to changes in pulmonary arterial pressure. Using the same injection protocol as in FIG. 13C, we measured pulmonary arterial pressures (PAPs) and found that while the positive control (GlyA) increased PAPs, RH did not at all compared to the negative control (RBCs without NCs).

Our final test of safety was to make sure RH does not worsen existing pathologies. We tested this in our mouse model of ARDS, intratracheal LPS. LPS markedly increased leukocytes (FIG. 13F, left panel) and edema-related protein in the alveoli (FIG. 13F, right panel), but the addition of RH did not lead to any change in these sensitive inflammatory markers.

Figure 14A:
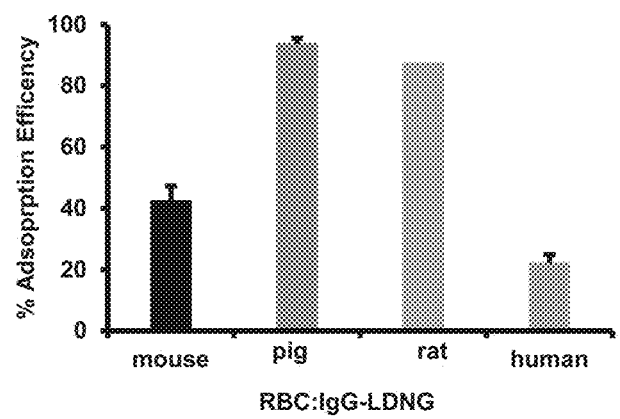
FIG. 14A shows that RBC-hitchhiking works in large animals and ex vivo human lungs. The bar graphs shows adsorption efficiency of nanogels onto various species' RBCs.

With the safety of RH tested in mice, we next sought to determine if RH worked in larger species. It was possible that RH only worked for the particular RBC and capillary properties found in mice. Therefore, we began by testing the first step of RH, NC adsorption onto RBCs. NC adsorption worked in mouse, rat, pig, and humans, though with a range of adsorption efficiencies (FIG. 14A).

Figure 14B:
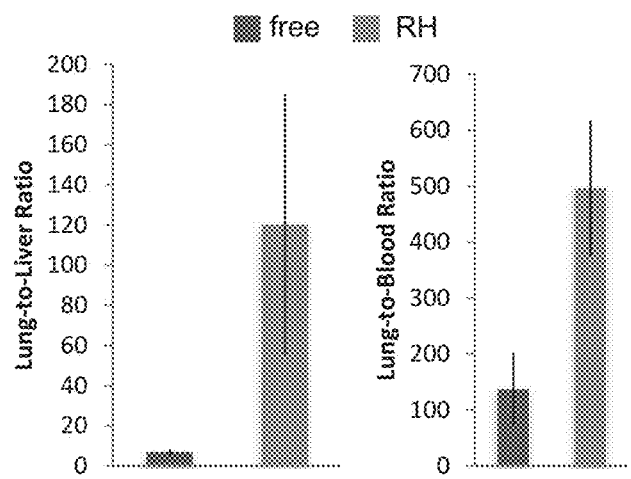
FIG. 14B shows the results of injecting live pigs with I-125 labeled nanogels that were either free (left bar in each panel) or RH (right bar in each panel). Plotted are the lung-to-live (left panel) and lung-to-blood ratios (right panel).
Figure 14C:
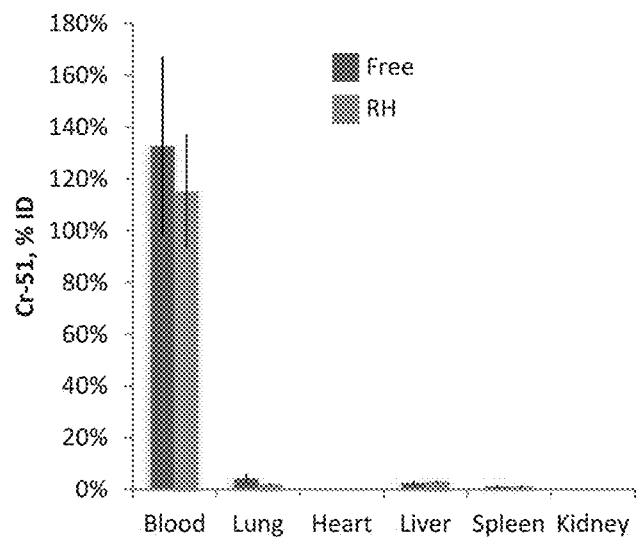
FIG. 14C is a graph showing the assessment of safety in pigs by showing that Cr51-labeled RBCs used in the RH experiments of FIG. 14B did not get stuck in the lungs.

Next we tested RH efficiency in vivo in a common large animal model, live pigs. IV injection of RH NCs led to a lung-to-liver ratio of 120 (FIG. 14B, left panel), meaning the concentration of NCs in the target organ of lungs (#NCs per gram of tissue) was 120× higher than the liver. That lung-to-liver ratio was 17-fold higher than seen with free NCs; an RH-to-free proportionality very similar to the equivalent value seen in mice (14.6×, FIG. 11C). Similar augmentation of lung targeting by RH in the pig was demonstrated by the lung-to-blood ratio of 490 (FIG. 14B, right panel). Importantly, as in mice, RH in pigs did not lead to RBCs themselves getting stuck in the lungs, as determined by the biodistribution of Cr-51-labeled RBCs (FIG. 14C). Notably, the data and FIGS. 14B and 14C were from the same individual pigs, with the RH NCs labeled with I-125 accumulating strongly in the lungs (FIG. 14B), while the Cr-51-labeled RBCs did not accumulate in the long, showing the RBCs are "dropping off" the NCs in the target organ in large animals.

Figure 14D:
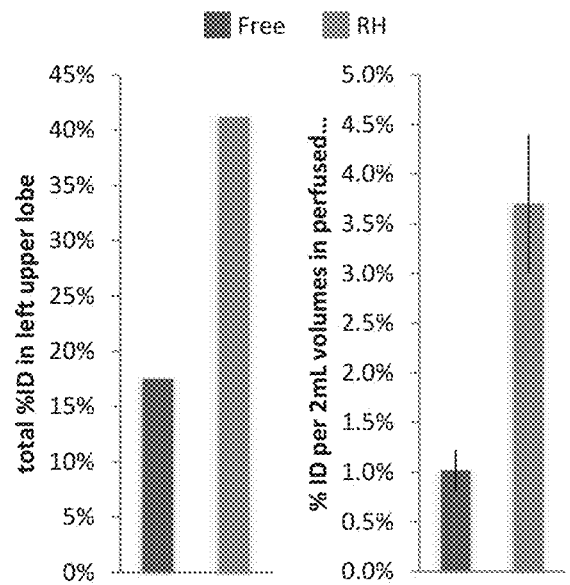
FIG. 14D shows the results of endovascularly cannulating ex vivo human lungs and then infusing same through a single artery sequentially with: I-125-labeled RH nanogels; I-131-labeled free nanogels; a green tissue dye. The graphs show percent of the injected dose of the entire lung lobe (left panel) and within only the well perfused zone (right panel, where 2 mL volumes were measured and their mean and SEM listed on the plot). Free nanogels, left bar in each panel; RH nanogels, right bar in each panel.

To extend the RH data from large animals to humans, we tested the effectiveness of RH in human lungs ex vivo. We obtained fresh human lungs from an organ donor whose lungs were deemed unsuitable for donation due to the presence of capillary leak and pulmonary edema similar to ARDS, the target lung disease for RH. Within 12 hours of organ donor death, we had endovascularly cannulated sub-segmental branches of the pulmonary artery (data not shown). Into one such artery, we infused both I-125-labeled NCs adsorbed onto RBCs and I-131-labeled NCs that were "free" (not adsorbed onto RBCs), followed by a green tissue dye to mark the infused tissue and prove perfusion to a single lung subsegment (data not shown). The reason to inject both the RH and free NCs into the same artery is that co-injection into a single vessel controls for differences in quality of endovascular cannulation/vessel isolation and the fact that ARDS pathology is patchy, which can affect NC uptake. As shown in FIG. 14D's left panel, 41% of the injected dose of RH NCs deposited in the entire lung. When the tissue was sub-divided into 2 mL volumes and only the top 10% best perfused volumes (judged by green tissue dye intensity) was included (FIG. 14D, right panel), it can be seen that RH resulted in 3.7× more deposition of NCs than free NCs. Notably, the background lung uptake of free NCs was much higher than found in mice, which may have been due to the severity of ARDS-like pathology and cold-ischemia time after transplant harvesting, which can cause severe capillary leak and microvascular clots. Nevertheless, RH clearly increased NCs to delivery to human lungs, in the setting of a pathology very similar to the goal clinical application of RH in the lungs.

Figure 15A:
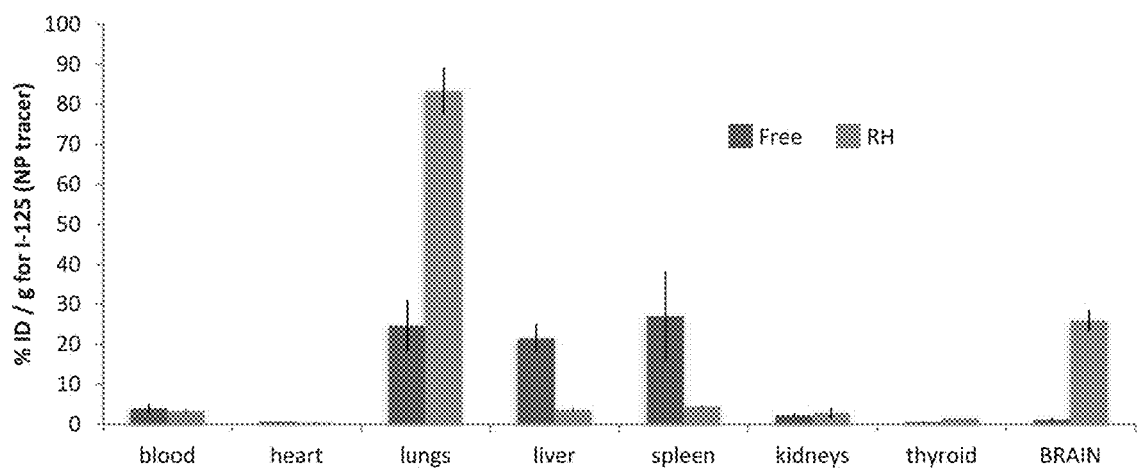
FIG. 15A is a graph showing that intra-arterial injections of RBC-hitchhiking NCs produce to very high brain uptake. Mice were anesthetized and had their right carotid artery cannulated. Into that intra-arterial cannula we injected either free (left dark bar in each set) or RH (right gray bar in each set) I-125-labeled nanogels, followed 30 minutes later by sacrifice and measurement of organs. Biodistribution is plotted as % ID/g.
Figure 15B:
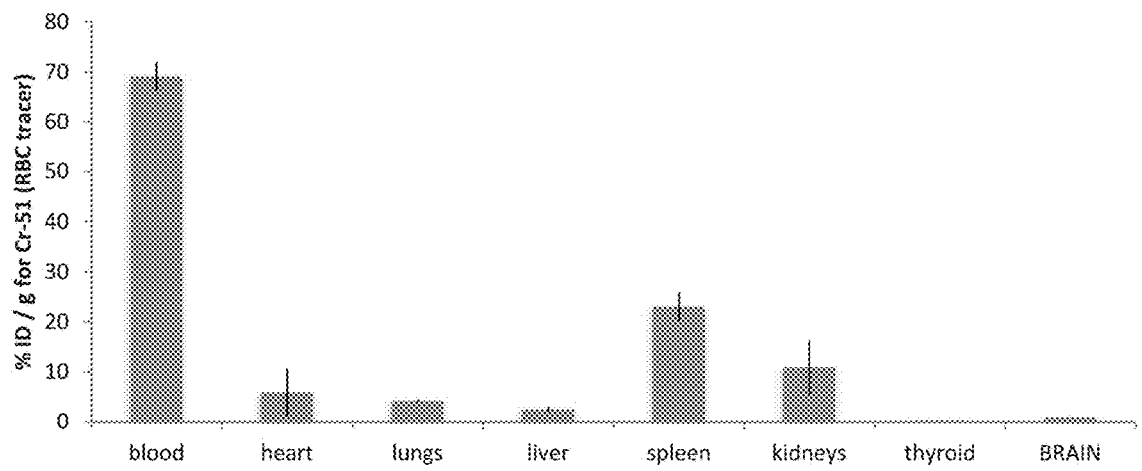
FIG. 15B shows that the RBCs of the RH nanogels were Cr51 labeled, and their biodistribution is listed as % ID/g.
Figure 15C:
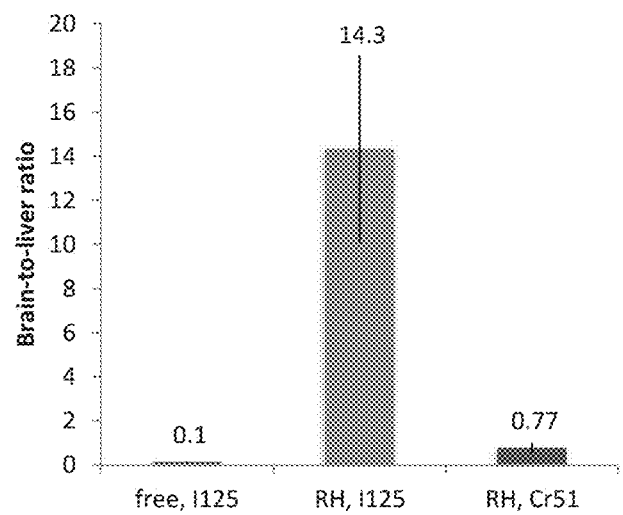
FIG. 15C shows the brain-to-liver ratios of the free nanogels, the I-125 signal of RH nanogels, and the Cr51 signal of the RBCs involved in RH (bars are labeled).
Figure 15D:
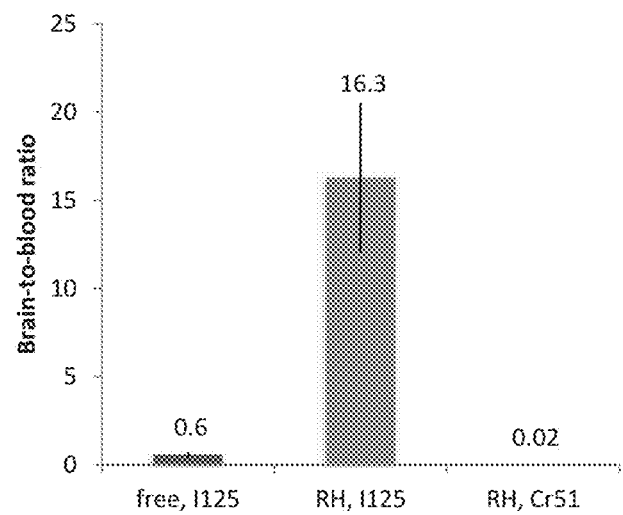
FIG. 15D shows the brain-to-lung ratios of the free nanogels, the I-125 signal of RH nanogels, and the Cr51 signal of the RBCs involved in RH (bars are labeled).

Having shown RH safely delivers NCs in multiple species, we next wanted to determine if RH could deliver NCs to multiple different target organs. We hypothesized that RH would target NCs to any organ immediately downstream of the injection catheter. Therefore, instead of injecting IV, we injected into the common carotid of mice, in order to target the brain. NCs were labeled with I-125 and RBCs with Cr-51. As seen in biodistribution of FIG. 15A, with RH, the brain uptake was 26% ID/gram, compared to 1.2% for free NCs, a 22-fold increase in brain uptake. Importantly, the brain uptake of Cr-51-labeled RBCs in the RH mice was very low compared to other organs (FIG. 15B), suggesting RBCs are not getting stuck in the brain. More impressively, the brain-to-liver ratio of RH was 14.3, which was 143-fold higher than for free NCs (FIG. 15C). Similarly, the brain-to-blood ratio of RH was 27-fold higher than for free NCs (FIG. 15D. Thus, combined with the IV injection data, we have shown that RH can very strongly concentrate NCs in any organ downstream of the injection catheter.

The above examples demonstrate that we have optimized and generalized the concept of RH, showing that optimized RH can safely and powerfully target NCs to any organ with an upstream intravascular catheter, without the need for an affinity moiety. It is notable that the magnitude of optimized RH's organ targeting significantly outperforms that of prior technologies, which all require affinity moieties. For example, anti-PECAM antibodies have been used for >20 years to target IV-injected ~100 nm NCs to the lungs, and we are unaware of any affinity moiety that achieves higher lung uptake for this size NC. In our study, anti-PECAM-nanogels had a lung-to-liver ratio 14.6× lower than that achieved by RH-nanogels without an affinity moiety. RH's advantage over prior technologies is even more pronounced in the brain. The best brain-targeting affinity moiety published so far is transferrin, and when highly optimized only delivered 1% of the injected dose (% ID) to brain[29], compared to RH-nanogels, which produced a brain uptake of 12% ID. These order-of-magnitude advantages of RH should greatly improve the risk-benefit ratios of delivered drugs.

The improved NC delivery and safety of RH resulted from several optimizations, but most notably the screening of NCs for optimal performance. While all NCs and viral vectors tested worked with RH, it is notable that by far the best performers, liposomes and nanogels, are also the softest (lowest shear modulus). Of course, different NC types have more differences than just their shear moduli. Therefore to prove optimal NC properties, future studies should use a single NC with tunable properties such as shear modulus.

The mechanism for RH was originally hypothesized to be that when NC-covered RBCs squeeze through capillaries, the NCs are transferred capillary endothelium. We provided the first experimental proof of this by showing via histological analysis that RH NCs are indeed found inside the capillary endothelial cells. Surprisingly, we also found that in pathological tissue, RH also delivers NCs strongly to intravascular leukocytes that reside in the capillaries. Consistent with this finding, in vitro macrophages in flow chambers grabbed RBCs and removed NCs coating them. In the lung pathology RH is best suited for, ARDS, both endothelial cells and local leukocytes are both prominent targets for treatment, so targeting both can have major advantages.

The efficient nature and mechanism RH raises the question of whether RH is recapitulating an evolved mechanism. For example, viruses may adsorb onto RBCs, as AAV did here, and then get taken up into the next organ to which they are presented. Notably, the NCs used here are in the same size range of most viruses (e.g., AAV is 25 nm and HIV 120 nm). The lung, as the first capillary bed after entry of a NC or pathogen into a vein, may have evolved the function of taking up RBC-adsorbed pathogens as a defense mechanism to protect other downstream organs. Future studies can elucidate the role of RBC adsorption and RH in pathogen uptake into organs.

Turning RH from a potential evolved mechanism into a therapy exploits 3 size ranges: nanoscale drug carriers; micron-scale RBCs that position the NCs within the vessel lumen; and macro-scale catheters that determine which organ's capillary bed receives delivery. This nano-micro-macro synergy provides tremendous target-organ specificity by focusing on delivery of NCs on the "first-pass" of the injectate through an organ. Such a system is now very practical for the most common acute, severe diseases. In severe heart attacks and embolic strokes, standard of care is to insert an intra-arterial (IA) catheter for removal of the flow blockage, thereby easily allowing IA injection of RH NCs. For the most common severe acute lung disease, ARDS, which accounts for 10% of all intensive care unit admissions (ICU), only an IV catheter is needed, which all such patients have in place. Thus, RH is well poised to serve as the delivery modality for the 3 most important acute, severe illnesses. Another major application, which also will utilize directing RH into macro-scale catheters, is delivery into transplanted organs, to deliver ischemia-reperfusion-injury drugs. Thus, RH has the potential to provide a drug delivery platform for multiple common diseases that currently lack effective therapies.

Each and every patent, patent application, and publication, including websites cited throughout specification, and the priority document U.S. Provisional Patent Application No. 62/403,764, filed Oct. 4, 2016, are incorporated herein by reference. While the invention has been described with reference to particular embodiments, it will be appreciated that modifications can be made without departing from the spirit of the invention. Such modifications are intended to fall within the scope of the appended claims.

REFERENCES

1. US patent application publication number 20110262466
2. US patent application number publication 20100285015
3. Brenner, J. S., et al, Endothelial nanomedicine for the treatment of pulmonary disease. Expert Opin. Drug Deliv. 12, 239-261 (2015).
4. Anselmo, A. C. et al., Delivering nanoparticles to lungs while avoiding liver and spleen through adsorption on red blood cells, ACS Nano, November 2013, 7(12): 11129-11137
5. Ferrer, M. C. C. et al., Icam-1 targeted nanogels loaded with dexamethasone alleviate pulmonary inflammation, PLoS One, July 2014, 9(7): e102329
6. U.S. Pat. No. 8,329,161
7. U.S. Pat. No. 8,734,787
8. US patent application publication number 20100061937
9. Harisa, G. I. et al., Pravastatin chitosan nanogels-loaded erythrocytes as a new delivery strategy for targeting liver cancer, Saudi Pharmaceutical Journal, January 2016, 24(1):74-81
10. Pan, D. et al., The Effect of Polymeric Nanoparticles on Biocompatibility of Carrier Red Blood Cells, PLOS One, March 2016, 11(3): e0152074
11. Tan, S. et al., Cell or Cell Membrane-Based Drug Delivery Systems[BG1] [BG2], Theranostics, April 2015, 5(8): 863-881
12. Luk, B. T. et al., Safe and Immunocompatible Nanocarriers Cloaked in RBC Membranes for Drug Delivery to Treat Solid Tumors, Theranostics, April 2016, 6(7):1004-1011
13. International Patent Application Publication No. WO2015179602
14. U.S. Pat. No. 4,652,449
15. Dimitrakopoulos et al, Squeezing Motion of Capsules and Erythrocytes in Microfluidic Channels and Vascular Capillaries
16. US patent application publication number 20110008304
17. US patent application publication number 20110268803
18. US patent application publication number 20110250134
19. Oral I, et al. "Measuring the Young's modulus of polystyrene-based composites by tensile test and pulse-echo method", Polymer Bull, 67(9):1893-1906 (December 2011)
20. Hwang M R et al., Gentamicin-Loaded Wound Dressing With Polyvinyl Alcohol/Dextran Hydrogel: Gel Characterization and In Vivo Healing Evaluation. AAPS PharmSciTech 2010; 11(3):1092-1103
21. Eckmann D M, et al., Nanogel Carrier Design for Targeted Drug Delivery. J Mater Chem B Mater Biol Med 2015; 2(46):8085-8097
22. Ahmed E M, March 2015, "Hydrogel: Preparation, Characterization, and Applications: A Review", J. Adv. Res., 6(2):105-121,
23. Brochu H, Vermette P. Young's Moduli of Surface-Bound Liposomes by Atomic Force Microscopy Force Measurements. Langmuir 2008; 24(5):2009-2014
24. Liang X, Mao G, Ng S. Mechanical properties and stability measurement of cholesterol-containing liposome on mica by atomic force microscopy. J Coll Interface Sci 2004; 278:53-62.
25. Dunér G, et al., "Quartz Crystal Microbalance with Dissipation (QCM-D) studies of the viscoelastic response from a continuously growing grafted polyelectrolyte layer." J Colloid Interface Sci. 2013 Oct. 15; 408:229-34
26. Scarcelli G, et al. Noncontact three-dimensional mapping of intracellular hydromechanical properties by Brillouin microscopy. Nature Methods 2015; 12:1132-1134.
27. Berkhemer, O A et al, "A Randomized Trial of Intraarterial Treatment for Acute Ischemic Stroke", N Engl J Med. 2015 Jan. 1; 372(1):11-20.
28. Gustafson, H. H., Holt-Casper, D., Grainger, D. W. & Ghandehari, H. Nanoparticle Uptake: The Phagocyte Problem. Nano Today 10, 487-510 (2015).
29. Wiley, D. T., Webster, P., Gale, A. & Davis, M. E. Transcytosis and brain uptake of transferrin-containing nanoparticles by tuning avidity to transferrin receptor. Proc. Natl. Acad. Sci. U.S.A. 110, 8662-8667 (2013).
30. Chu, D. et al. Nanoparticle Targeting of Neutrophils for Improved Cancer Immunotherapy. Adv. Healthc. Mater. 5, 1088-1093 (2016).

31. Anselmo, A. C. & Mitragotri, S. Cell-mediated delivery of nanoparticles: taking advantage of circulatory cells to target nanoparticles. J. Control. Release 190, 531-541 (2014).
32. Hood, E. D. et al. Antioxidant protection by PECAM-targeted delivery of a novel NADPH-oxidase inhibitor to the endothelium in vitro and in vivo. J. Control. Release 163, 161-169 (2012).
33. Brenner, J. S. et al. Mechanisms that determine nanocarrier targeting to healthy versus inflamed lung regions. Nanomedicine (2017). doi:10.1016/j.nano.2016.12.019
34. Pan, D. et al. The Effect of Polymeric Nanoparticles on Biocompatibility of Carrier Red Blood Cells. PLoS One 11, e0152074 (2016).
35. Kuebler, W. M. & Goetz, A. E. The marginated pool. Eur. Surg. Res. 34, 92-100 (2002).
36. Schneberger, D., Aharonson-Raz, K. & Singh, B. Pulmonary intravascular macrophages and lung health: what are we missing? Am. J. Physiol. Lung Cell. Mol. Physiol. 302, L498-503 (2012).
37. Armstead, W. M. et al. RBC-coupled tPA Prevents Whereas tPA Aggravates JNK MAPK-Mediated Impairment of ATP- and Ca-Sensitive K Channel-Mediated Cerebrovasodilation After Cerebral Photothrombosis. Transl. Stroke Res. 3, 114-121 (2012).

The invention claimed is:

1. A method for delivering a drug to a selected organ or tissue of a mammalian subject having a disease, the method comprising intravenously or intraarterially administering to the subject a composition comprising a red blood cell having nanoparticles physisorbed thereto, said nanoparticles having a shear modulus or Young's modulus of less than 10 MPa and containing a drug, wherein following administration of the composition said nanoparticles are transferred from the red blood cell to the vascular cells of a first capillary bed encountered downstream of the site of intravenous or intraarterial administration, said capillary bed being in the selected organ or tissue, and wherein said nanoparticles release the drug for delivery of the drug to said selected organ or tissue.

2. The method according to claim 1, wherein the nanoparticles are characterized by having at least one of
   (a) a shear modulus of less than 1 MPa;
   (b) a hydrophilic exterior;
   (c) a coating with a biomolecule that does not induce an immunological reaction to the composition in a mammalian subject;
   (d) a globular shape with a diameter of about 10 to 1000 nm; and
   (e) no cell-specific targeting moiety or tissue-specific targeting moiety or organ-specific targeting moiety associated therewith.

3. The method according to claim 2, wherein said biomolecule is a protein or albumin or IgG.

4. The method according to claim 1, wherein the nanoparticles are hydrogels or liposomes.

5. The method according to claim 4, wherein said hydrogel nanoparticles are synthetic constructs of lysozyme and dextran or wherein the hydrogel nanoparticles are about 300 nm in size.

6. The method according to claim 1, wherein the nanoparticles are miscible with endothelial glycocalyx or are characterized by release kinetics permitting greater than 50% of the drug load to be released within about 1 hour after administration in vivo.

7. The method according to claim 1, wherein said drug is a water miscible compound.

8. The method according to claim 1, wherein said nanoparticles are hydrogels containing a water-miscible drug selected from one or more of albuterol, dexamethasone, and palifermin.

9. The method according to claim 8, wherein the nanoparticles are lysozyme-dextran hydrogels, optionally coated with albumin or IgG.

10. The method according to claim 1, wherein said drug is released from the nanoparticles within 60 minutes of administration.

11. The method according to claim 1, wherein the selected target organ is the lungs.

12. The method according to claim 1, wherein
   (a) the disease is ARDS, pneumonia, interstitial lung disease, idiopathic pulmonary fibrosis, post-pulmonary embolism; pulmonary capilliaritis syndrome, or emphysema; or
   (b) said disease is ARDS and wherein said drug is one of more of albuterol, dexamethasone, and palifermin.

13. The method according to claim 1, further comprising rotating or agitating said composition before administering to prevent settling and aggregation of red blood cells.

14. The method according to claim 1, wherein said drug is a therapeutic drug, a prophylactic drug, an imaging or diagnostic drug, an anti-rejection drug, an anti-inflammatory agent, a pro-angiogenic factor, an anti-edema agent, or an agent that prevents ischemia-reperfusion injury.

15. A method for delivering a drug to a selected organ or tissue of a mammalian subject, the method comprising administering via intra-arterial catheter to the subject a composition comprising a red blood cell having nanoparticles physisorbed thereto, said nanoparticles having a shear modulus or Young's modulus of less than 10 MPa and containing a drug, wherein following administration of the composition said nanoparticles are transferred from the red blood cell to the vascular cells of a first capillary bed encountered downstream of the intra-arterial catheter, said first capillary bed being in the selected organ or tissue, and wherein said nanoparticles release the drug for delivery of the drug to said selected organ or tissue.

16. The method according to claim 15, wherein said drug is a water miscible compound.

17. The method according to claim 15, wherein said nanoparticle is a hydrogel containing a water-miscible drug selected from one or more of albuterol, dexamethasone and palifermin.

18. The method according to claim 15, wherein the selected organ is the brain or heart.

19. A method for delivering a drug to a selected organ designated for transplantation, the method comprising administering to the organ ex vivo, via intraarterial or intravenous injection, a composition comprising a red blood cell having nanoparticles physisorbed thereto, said nanoparticles having a shear modulus or Young's modulus of less than 10 MPa and containing a drug, wherein following administration of the composition said nanoparticles are transferred from the red blood cell to the vascular cells of a first capillary bed encountered downstream of the site of administration, and wherein said nanoparticles release the drug for delivery of the drug to the selected organ.

* * * * *